United States Patent [19]

Tracy et al.

[11] Patent Number: 5,721,265
[45] Date of Patent: Feb. 24, 1998

[54] FLUORINATED 2-NITROIMIDAZOLE ANALOGS FOR DETECTING HYPOXIC TUMOR CELLS

[75] Inventors: Michael Tracy, Palo Alto; Andrew B. Kelson, San Carlos, both of Calif.; Paul Workman, Wilmslow, England; Alexander D. Lewis; Eric O. Aboagye, both of Bearsden, Scotland

[73] Assignee: SRI International, Menlo Park, Calif.

[21] Appl. No.: 458,178

[22] Filed: Jun. 2, 1995

Related U.S. Application Data

[63] Continuation-in-part of Ser. No. 286,477, Aug. 5, 1994, abandoned.

[51] Int. Cl.$^6$ .................. C07D 233/02; C07D 233/04; C07D 233/54; C07D 233/28; C07D 233/68; A61K 31/415

[52] U.S. Cl. .................. 514/396; 514/397; 514/398; 514/400; 514/401; 548/311.1; 548/327.5; 548/342.5

[58] Field of Search .................. 514/396, 397; 548/311.1

[56] References Cited

U.S. PATENT DOCUMENTS

| | | | |
|---|---|---|---|
| 3,679,698 | 7/1972 | Beaman et al. | 548/327.5 |
| 4,977,273 | 12/1990 | Kagiya et al. | 548/327.5 |
| 5,304,654 | 4/1994 | Kagiya et al. | 548/327.5 |

FOREIGN PATENT DOCUMENTS 0 294 847  12/1988  European Pat. Off. .

OTHER PUBLICATIONS

Brown et al., "Partition Coefficient as a Guide to the Development of Radiosensitizers Which are Less Toxic than Misonidazole," *Radiation Res.* 82:171–190 (1980).

Brown et al., "SR-2508: A 2-Nitroimidazole Amide which Should Be Superior to Misonidazole as a Radiosensitizer for Clinical Use," *Int. J. Rad. Oncol. Biol. Phys.* 7:695–703 (1981).

Dabrow et al., "Molecular Dimensions and Properties of N-[1-(2-Hydroxyethyl)-2-nitro-1H-imidazol-1-yl]acetamide," *Arch. Biochem. Biophys.* 302:259–264 (1993).

Evelhoch et al., "A Method for Direct in Vivo Measurement of Drug Concentrations from a Single $^2$H NMR Spectrum," *Magn. Reson. Med.* 9:402–410 (1989).

Jin et al., "Dynamic measurements of hexafluoromisonidazole (CCI–103F) retention in mouse tumours by $^1$H/$^{19}$F magnetic resonance spectroscopy," *Int. J. Radiation Biol.* 58:1025–1034(1990).

Kwock et al., "Evaluation of a Fluorinated 2–Nitroimidazole Binding to Hypoxic Cells in Tumor–Bearing Rats by $^{19}$F Magnetic Resonance Spectroscopy and Immunohistochemistry," *Radiation Res.* 129:71–78 (1992).

Li et al., "Prediction of Tumor Radiosensitivity by Hexafluoromisonidazole Retention Monitored by [$^1$H]/[$^{19}$F] Magnetic Resonance Spectroscopy," *Cancer Comm.* 3:133–139 (1991).

Mannan et al., "Radioiodinated 1–(2–Fluoro–4–iodo–2, 4–dideoxy–β–L–xylopyranosyl)–2–nitroimidazole: A Novel Probe for the Noninvasive Assessment of Tumor Hypoxia," *Radiation Res.* 132:368–374 (1992).

Mashiba et al., "Enhancement of Radiosensitizing Effect of the Nitroimadazole Derivative RK28 on the Proliferation of MethA Tumor Cells in Combined Use with Diethyldithiocarbamate," *Life Sciences* 49:1419–142A5 (1991).

Maxwell et al., "Demonstration of Tumor–Selective Retention of Fluorinated Nitroimadazole Probes by $^{19}$F Magnetic Resonance Spectroscopy in Vivo," *Int. J. Radiation Oncol. Biol. Phys.* 16:925–929 (1989).

Murayama et al., "Radiosensitization by a New Nucleoside Analogue: 1–[2–Hydroxy–1–(Hydroxymethyl)ethoxy] methyl–2–Nitroimidazole (RP–170)," *Int. J. Radiation Oncol. Biol. Phys.* 17:575–581 (1989).

Raleigh et al., "Development of an in Vivo $^{19}$F Magnetic Resonance Method for Measuring Oxygen Deficiency in Tumors," *Magn. Reson. Med.* 22:451–466 (1991).

Raleigh et al., "Covalent binding of a Fluorinated 2–Nitroimidazole to EMT–6 Tumors in Balb/C Mice: Detection by F–19 Nuclear magnetic Resonance at 2.35 T," *Int. J. Radiation Oncol. Biol. Phys.* 12:1243–1245 (1986).

Sasai et al., "A Fluorinated 2–Nitroimidazole, KU–2285, as a New Hypoxic Cell Radiosensitizer," *Int. J. Radiation Oncol. Biol. Phys.* 20:1249–1254 (1991).

Sasai et al., "In Vivo Radiosensitizing Activity of a New Fluorinated Hypoxic Cell Radiosensitizer, KU–2285, in Combination with Radiation Dose Fractionation," *Int. J. Radiation Oncol. Biol. Phys.* 21:1231–1234 (1991) (last page missing).

Shibamoto et al., "Radiosensitization efficacy of KU–2285, RP–170 and etanidazole at low radiation doses: assessment by in vitro cytokinesis–block micronucleus assay," *Int. J. Radiation Biol.* 61:473–478 (1992).

Shibamoto et al., "Evaluation of a new 2–nitroimidazole nucleoside analogue, RK–28 as a radiosensitizer for clinical use," *Int. J. Radiation Biol.* 59:105–115 (1991).

(List continued on next page.)

*Primary Examiner*—Floyd D. Higel
*Attorney, Agent, or Firm*—Dianne E. Reed; Bozicevic & Reed LLP

[57] ABSTRACT

Agents useful for detecting hypoxic tumor cells are provided. The compounds have the structural formula (I)

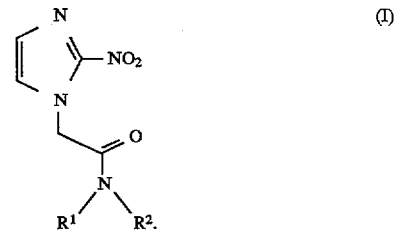

Methods of using the compounds to detect hypoxic tumor cells are also provided, as are pharmaceutical compositions formulated with the novel compounds.

47 Claims, 8 Drawing Sheets

OTHER PUBLICATIONS

Shibamoto et al., "Characterisitcs of Fluorinated Nitroazoles as Hypoxic Cell Radiosensitizers," *Int. J. Radiation Oncol. Biol. Phys.* 16:1045–1048 (1989).

Workman et al., "Non–invasive MRS in New Anticancer Drug Development," *NMR Biomed.* 5:270–272 (1992).

Workman et al., "Structure–pharmacokinetic Relationships for Misonidazole Analogues in Mice," *Cancer Chemother. Pharmacol.* 6:39–49 (1981).

Jin et al., "Dynamic measurements of hexafluoromisonidazole (CCI–103F) retention in mouse tumours by $^1H/^{19}F$ magnetic resonance spectroscopy" *(1990) Int. J. Radiation Biol.* 58:1025–1034.

Kwock et al., "Evaluation of a Fluorinated 2–Nitroimadazole Binding to Hypoxic Cells in Tumor–Bearing Rats by $^{19}F$ Magnetic Resonance Spectroscopy and Immunohistochemistry" (1992) *Radiation Res.* 129:71–78.

Li et al., "Prediction of Tumor Radiosensitivity by Hexafluoromisonidazole Retention Monitored by $[^1H]/[^{19}F]$ Magnetic Resonance Spectroscopy" (1991) *Cancer Comm.* 3:133–139.

Mannan et al., "Radioiodinated 1–(2–Fluoro–4–iodo–2, 4–dideoxy–/β–L–xylopyranosyl)–2–nitroimidazole: A Novel Probe for the Noninvasive Assessment of Tumor Hypoxia" (1992) *Radiation Res.* 132:368–374.

Mashiba et al., "Enhancement of Radiosensitizing Effect of the Nitroimadazole Derivative RK28 on the Proliferation of MethA Tumor Cells in Combined Use with Diethyldithiocarbamate" (1991) *Life Sciences* 49:1419–1425.

Maxwell et al, "Demonstration of Tumor–Selective Retention of Fluorinated Nitroimadazole Probes by $^{19}F$ Magnetic Resonance Spectroscopy in Vivo" (1989) *Int. J. Radiation Oncol. Biol. Phys.* 16:925–929.

Murayama et al., "Radiosensitization by a New Nucleoside Analogue: 1–[2–Hydroxy–1–(Hydroxymethyl)ethoxy] methyl–2–Nitroimidazole (RP–170)" (1989) *Int. J. Radiation Oncol. Biol. Phys.* 17:575–581.

Raleigh et al. "Development of an in Vivo $^{19}F$ Magnetic Resonance Method for Measuring Oxygen Deficiency in Tumors" (1991) *Magn. Reson. Med.* 22:451–466.

Raleigh et al., "Covalent binding of a Fluorinated 2–Nitroimidazole to EMT–6 Tumors in Balb/C Mice: Detection by F–19 Nuclear magnetic Resonance at 2.35 T" (1986) *Int. J. Radiation Oncol. Biol. Phys.* 12:1243–1245.

Sasai et al., "A Fluorinated 2–Nitroimidazole, KU–2285, as a New Hypoxic Cell Radiosensitizer" (1991) *Int. J. Radiation Oncol. Biol. Phys.* 20:1249–1254.

Sasai et al., "In Vivo Radiosensitizing Activity of a New Fluorinated Hypoxic Cell Radiosensitizer, KU–2285, in Combination with Radiation Dose Fractionation" (1991) *Int. J. Radiation Oncol. Biol. Phys.* 21:1231–1234.

Shibamoto et al., "Radiosensitization efficacy of KU–2285, RP–170 and etanidazole at low radiation doses: assessment by in vitro cytokinesis–block micronucleus assay" (1992) *Int. J. Radiation Biol.* 61:473–478.

Shibamoto et al., "Evaluation of a new 2–nitroimidazole nucleoside analogue, RK–28 as a radiosensitizer for clinical use" (1991) *Int. J. Radiation Biol.* 59:105–115.

Shibamoto et al., "Characterisitcs of Fluorinated Nitroazoles as Hypoxic Cell Radiosensitizers" (1989) *Int. J. Radiation Oncol. Biol. Phys.* 16:1045–1048.

Workman et al., "Non–invasive MRS in New Anticancer Drug Development" (1992) *NMR Biomed.* 5:270–272.

Workman et al., "Structure–pharmacokinetic Relationships for Misonidazole Analogues in Mice" (1981) *Cancer Chemother. Pharmacol.* 6:39–49.

Maxwell et al., "Demonstration of Tumor–Selective Retention of Fluorinated Nitroimidazole Probes by Florine–19 Magnetic Resonance Spectroscopy In Vivo," *Chemical Abstracts* 111(7):53409g (1989) (see also, *Int. J. radiat. Oncol., Biol. Phys.* 16(4):925–9 (1989).

FLUORINATED 2-NITROIMIDAZOLE ANALOGS FOR DETECTING HYPOXIC TUMOR CELLS

CROSS-REFERENCE TO RELATED APPLICATIONS

This application is a continuation-in-part of U.S. patent application Ser. No. 08/286,477, filed Aug. 5, 1994, now abandoned.

TECHNICAL FIELD

The present invention relates generally to compounds useful for detecting hypoxic tumor cells, and more particularly relates to certain novel tumor detecting compounds. The invention also relates to methods and pharmaceutical compositions for detecting hypoxic tumor cells.

BACKGROUND

Oxygen provides the major source of cellular energy through oxidative phosphorylation. Tissue hypoxia occurs when oxygen supply to cells is inhibited and may occur in vascular disease, during a stroke or in tumors. Hypoxic tumor cells are therefore those existing at an intermediate oxygen tension between well-oxygenated cells (oxic population) and those with insufficient oxygen to support viability (anoxic population); cells existing at an oxygen partial pressure ($pO_2$) of 0.1% or less are referred to as radiobiologically hypoxic cells. Structural and functional abnormalities of tumor vasculature and microcirculation may account for the existence of hypoxic cells. Vaupel et al. (1989) *Cancer Res.* 49:6449–6465.

Hypoxia in tumors may be present in irreversible diffusion limited ("chronic") form or in reversible perfusion limited ("acute") form. Brown (1979) *Br. J. Radiol.* 52:650–656; Minchinton et al. (1993) in *8th International Conference on Chemical Modifiers of Cancer Treatment*, Kyoto, Japan, 192–193; Thomlinson et al. (1955) *Br. J. Cancer* 9:539–549. Chronic hypoxia, the classic model of tumor hypoxia, arises when solid tumors outgrow their supportive vasculature. The diffusion distance of molecular oxygen is limited by metabolic consumption to 150–200 µm from the nearest capillary. Beyond the diffusion distance, cells are necrotic. Immediately proximal to the necrotic zone is a layer of cells which are oxygen deprived yet viable. These cells are the result of a diffusion limitation of oxygen and remain hypoxic until they become either re-oxygenated or die, and hence are referred to as chronically hypoxic cells. They are also likely to have low levels of glucose and ATP, and high levels of catabolites such as lactate. Vaupel (1992) *NMR Biomed.* 5:220–225.

If blood flow through a vessel is transiently stopped then all the normally aerobic cells down-stream of the occlusion are suddenly made hypoxic. These cells are considered acutely hypoxic because they only remain hypoxic as long as the occlusion continues, becoming oxygenated again when blood flow resumes. Currently available information on the parameters defining the metabolic micromilieu in human tumors indicates that significant variations in these relevant factors are likely to occur between different locations within a tumor and between tumors of the same grading and clinical staging. Vaupel (1992), supra.

Historically, the existence of hypoxic cells has significant implications for the treatment of cancer, i.e., with respect to radioresistance, chemoresistance, gene amplification and induction and overexpression of certain cellular or stress proteins. Hypoxic cells are known to be two to three times more resistant to cell killing by radiation as compared with oxic cells. Coleman (1988) *J. Natl. Cancer Inst.* 80:310–317; Hall (1988) in, Hall (Ed.), *Radiobiology for Radiologist*, Lippencott Co., Philadelphia, 137–160. This arises because, in cells at normal oxygen tension, molecular oxygen is able to interact with radiation-induced radicals in DNA, leading to irreversible fixation of the damage. Hall (1988), supra. According to the radiochemical competition model, molecular oxygen competes with reducing species, e.g., thiols such as glutathione, which are able to restore the target molecule to the original undamaged form. Hall (1988), supra. Since hypoxic cells do not possess sufficient molecular oxygen levels to compete effectively with reducing species, much of the radiation-induced damage in these cells is repaired.

Hypoxic cells are also resistant to a range of chemotherapeutic drugs, including bleomycin and several alkylating agents. Workman (1983) *Cancer Topics* 4:54–55. This may arise through impaired drug delivery, the induction of a non-cycling cell kinetic status or the involvement of molecular oxygen in the mechanism of action of the drug. Exposure of cells to hypoxia may also lead to the expression of new proteins. These include vascular endothelial growth factor, erythropoietin, oxygen- and glucose-regulated proteins and stress proteins such as heat shock transcription factor. Giaccia et al. (1992) *Int. J. Radiation Oncol. Biol. Phys.* 23:891–897; Semenza et al. (1992) *Mol. Cell. Bio.* 12:5447–5454; Shweiki et al. (1992) *Nature* 359:843–845; Heacock et al. (1986) *Int. J. Radiation Oncol. Biol. Phys.* 12:1287–1290. Relatively transient hypoxia can lead to an enhanced frequency of dihydrofolate reductase gene amplification and hence to methotrexate resistance. Rice et al. (1986) *Proc. Natl. Acad. Sci. USA* 83:5978–5982. Hypoxia-induced drug resistance is, however, different from P-glycoprotein associated multi-drug resistance. Sakata et al. (1991) *Br. J. Cancer* 64:809–814. The negative effects hypoxic cells have on clinical anti-tumor therapy has led to intensive research to identify these cells in tumors.

The $pO_2$ of venous blood is approximately 5%, thus providing nearly full radiation sensitivity. The oxygen tension at which cells display sensitivity midway between those in nitrogen and those in air or pure oxygen is around 0.5% ($K_m$ value). This implies that specific oxygen levels far below those encountered in normal tissues need to be measured accurately. However current technology often yields an average value for large numbers of neighboring cells and does not meet this need. This is a severe impediment for detection and diagnosis because histological evaluation of solid tumors suggests that important changes in cellular oxygen can occur over dimensions of even a few cell diameters. Urtasun et al. (1986) *Int. J. Radiation Oncol. Biol. Phys.* 12:1263–1267.

2-Nitroimidazoles have been under investigation as probes for tumor hypoxia, in part because of their ability to specifically label hypoxic cells, providing cellular resolution, and in part because of their sensitivity to accurately monitor the aforementioned low $pO_2$ values. The compounds are known to undergo nitroreduction to form reactive intermediates, such as hydroxylamines, which irreversibly bind to macromolecules in hypoxic tissues. Chapman et al. (1983) *Cancer Res.* 43:1523–1528; Koch et al. (1984) *Int. J. Radiation Oncol. Biol. Phys.* 10:1327–1332; Miller et al. (1982) *Int. J. Radiation Oncol. Biol. Phys.* 8:741–744; Taylor et al. (1978) *Cancer Res.* 38:2745–2752; Varghese et al. (1980) *Cancer Res.* 40:2165–2169. The rate of bioreduction increases with decreasing $pO_2$, allowing the labelling of hypoxic cells in preference to normal oxygen-rich cells including those of the adjacent stromal tissue. Urtasun et al. (1986), supra. This phenomenon has therefore been exploited in the development of markers for both invasive (by biopsy) and non-invasive evaluation of tumor hypoxia. Invasive procedures rely on biopsy samples which may not be representative of the whole tumor or require a detailed knowledge of the histological structure and vascular pattern of the tumor of interest; however, non-invasive techniques have the potential to allow the measurement of the oxygenation status of the tumor as a whole.

2-Nitroimidazoles bearing various radiolabels such as $^3$H, $^{14}$C, $^{18}$F, $^{82}$Br and $^{125}$I have been detected by autoradiography, liquid scintillation and gamma scintillation. Chapman (1984) *Cancer* 54:2441–2449; Koh et al. (1991) *Int. J. Radiation Oncol. Biol. Phys.* 22:199–212; Mannan et al. (1992) *Radiation Res.* 132:368–374; Rasey et al. (1982) *Radiation Res.* 91:542–554; Rasey, et al. (1985) *Radiation Res.* 102:76–85; Urtasun et al. (1986), supra. For example, melanomas, squamous cell carcinomas and small cell lung cancers in humans have been screened for their oxygenation status by Chapman and co-workers using liquid scintillation and autoradiography of histological sections. Chapman (1991) *Radiother. Oncol.* 20(Supp.):13–19. However, while these procedures show the potential of 2-nitroimidazoles to act as specific markers for hypoxic cells, they are not suitable for routine use because of the large doses of labelled marker required and the associated radiation dose or contamination. Additionally, instability of labels and accumulation of marker in certain other tissues limits their use. Chapman (1991), supra; Rasey et al. (1982), supra.

Several studies on the oxygenation status of tumors have been carried out using immunohistochemical methods, in particular, by employing the intrinsic fluorescence of nitroimidazole adducts or by means of fluorescent polyclonal and monoclonal antibodies directed against the adducts. 2-Nitroimidazoles containing fluorescent side chains such as theophylline, as well as other fluorescent nitroheterocycles such as trans-5-amino-3-[(5-nitro-2-furyl) vinyl]-1,2,4-oxadiazole, have been quantified in histological sections using flow cytometry. Hodgkiss et al. (1991) *Br. J. Cancer* 63:119–125; Olive et al. (1983) *Cancer Res.* 43:3276–3280. In addition fluorescent cell sorting provides a means of verifying the oxygenation status on a cell to cell basis. Polyclonal antibodies to the hexafluorinated 2-nitroimidazole CCI-103F and monoclonal antibodies to the pentafluorinated 2-nitroimidazole EF5 have recently been employed to study the oxygenation status of spheroids and experimental animal tumors. Lord et al. (1993) *Cancer Res.* 53:5721–5726; Raleigh et al. (1994) *Br. J. Cancer* 69:66–71; Raleigh et al. (1987) *Br. J. Cancer* 56:395–396. Apart from data on the oxygenation status of individual cells, these antibody techniques may provide additional data on sites of binding and even individual macromolecular adducts. However, as with other invasive techniques, they are limited by the biopsy size and would therefore again not completely account for the heterogeneity of the tumor as a whole.

2-Nitroimidazoles labelled with a positron emitter such as $^{18}$F can be detected non-invasively by positron emission tomography (PET). For instance, Koh et al. (1991), supra, have demonstrated the existence of hypoxic areas in tumors of patients prior to radiotherapy using PET imaging. In the study, hypoxic elements within a tumor volume were defined as regions with a threshold regional tumor:plasma $^{18}$F Misonidazole ratio $\geq 1.4$ by 2 or more hours post-injection. PET is a highly sensitive technique, however it suffers from major drawbacks such as short half-life of the $^{18}$F label ($t_{1/2} \approx 109.7$ min.) which results in considerable investment in technical facilities such as an on-site cyclotron needed to produce the labelled compounds immediately before use in the treatment facility. Studies may also be characterized by radiation exposure and lack of adequate chemical information.

Studies are in progress to develop γ-labelled 2-nitroimidazoles as non-invasive probes for tumor hypoxia by conventional nuclear medicine and single-photon emission tomography. For instance, Rasey and co-workers have studied the radiobiological and pharmacological properties of 4-bromomisonidazole as a marker for tumor hypoxia. Rasey et al. (1982), supra. Also Parliament and co-workers have employed $^{123}$I-iodoazomycin arabinoside as a probe for tumor hypoxia by single-photon emission tomography (SPECT). Parliament et al. (1992) *Br. J. Cancer* 65:90–95. Studies are still underway to fully evaluate the potential of this technique for clinical use.

It has now been extensively shown that 2-nitroimidazoles containing $^2$H and $^{19}$F labels(s) can be detected non-invasively in tumors by magnetic resonance spectroscopy (MRS) and imaging (MRI). Evelhoch et al. (1989) *Magn. Reson. Med.* 9:402–410; Jin et al. (1990) *Int. J. Radiation Biol.* 58:1025–1034; Kwock et al. (1992) *Radiation Res.* 129:71–78; Maxwell et al. (1989) *Int. J. Radiation Oncol. Biol. Phys.* 16:925–929; Raleigh et al. (1991) *Magn. Reson. Med.* 22:451–466; Raleigh et al. (1986) *Int. J. Radiation Oncol. Biol. Phys.* 12:1243–1245. Magnetic resonance spectroscopy is a technique which, similar to nuclear magnetic resonance, displays the signal obtained from the nucleus of interest as an intensity peak. This is in contrast to magnetic resonance imaging which displays the data as an image/picture or map of the intensity values. These techniques are becoming increasingly popular because of the widespread availability of MR facilities in most hospitals and because they use non-radioactive probes. The $^{19}$F nucleus is ideally suited for MRS studies because it has a spin of ½, a high natural abundance (100%), a relatively high sensitivity for detection (0.83 relative to protons) and low background. In general, the use of $^{19}$F MRS will depend on:

a) The availability of a fluorinated drug. 2-Nitroimidazoles with a high number of magnetically equivalent fluorines will generally give higher sensitivity. The compound should ideally have a relatively low lipophilicity and be relatively stable to loss of label through metabolic or non-metabolic processes.

b) The toxicity of the agent. Generally, only drugs which can be given in relatively high doses (on the order of 0.1 mmol/Kg/magnetically equivalent fluorine atom) can be detected at present. Workman et al. (1992) *NMR Biomed.* 5:270–272. This is influenced by the toxicity of the compounds, which is in turn related to their lipophilicities.

c) The pharmacokinetic properties of the compound and in particular the ratio of tumor tissue to normal tissue ratio. Apart from influencing the toxicity of the compounds these properties also show the specificity of the probes for the phenomenon of interest.

Using $^{19}$F MRS, two fluorinated Misonidazole analogues, Ro 07-0741 and CCI-103F, have been shown to be selectively retained in mouse tumors. Maxwell et al. (1989), supra; Workman et al. (1992), supra. Signal intensities were observed to be higher in EMT-6 and KHT than RIF-1 tumors and this was consistent with the known hypoxic fractions and comparative in vivo nitroreductase activity. Moulder et al. (1984) *Int. J. Radiation Oncol. Biol. Phys.* 10:695–712; Walton et al. (1987) *Biochem. Pharmacol.* 36:887–896. In another study, the $^{19}$F signal obtained from tumors following intraperitoneal injection of tumor-bearing rats with CCI-103F remained detectable in 4 of 10 rats after twenty-four hours, indicating possible nitroreductive bioactivation by hypoxic cells. Kwock et al. (1992), supra. Immunohistochemical assessment of these tumors revealed some staining for bound drug at the periphery of necrotic zones. Kwock et al. (1992), supra.

The viability of the MRI/MRS approach for the detection of tumors in vivo has been demonstrated by Maxwell et al. (1989), supra, using $^{19}$F labeled analogs of Misonidazole, CCI-103F and Ro 07-0741, and by Prior et al. (1990) *Biochem. Pharmacol.* 39:857–863 using 5-fluorouracil (5-FU). Recent work by Glaholm et al. (1990) *Br. J. Radiol.* 63:547–553 with patients receiving 5-FU treatment for recurrent gastrointestinal adenocarcinoma has also established that MRI/MRS techniques may be useful in monitoring the pharmacokinetics of suitably labeled compounds in vivo. Such methods have the potential for more enabling design of more precise treatment schedules for individual patients.

Although CCI-103F is superior to Ro 07-0741 in terms of magnetic resonance sensitivity, its clinical usefulness may be limited by its lipophilicity (octanol/water partition coefficient of CCI-103F=20; that of Ro 07-0741=0.41) and hence its toxicity. Like Misonidazole, CCI-103F is also susceptible to metabolic dealkylation with loss of the $^{19}$F label. This may contribute to non-oxygen-dependent variations in covalent adduct formation as well as difficulty in the interpretation of retention data.

The major problems with the $^{19}$F-labelled compounds utilized to date for MRI and MRS techniques are their neurotoxic side effects due to their relatively high lipophilicities (CCI-103F and Ro 07-0741) and a relatively weak signal due to the number of fluorine atoms per molecule (e.g., as found with 5-FU).

Therefore, although these compounds show significant potential, there is a definite need in the art for more site-specific and less toxic $^{19}$F tumor detecting agents with high signal strength.

Overview of Related Art

In addition to the publications cited in the preceding section, the following references are of interest as they relate to N-substituted 2-nitroimidazole derivatives:

U.S. Pat. No. 3,679,698 to Beaman et al. describes N-alkanoic acid amide derivatives of 2-nitroimidazole derivatives.

U.S. Pat. No. 4,977,273 to Kagiya et al. describes 2-nitroimidazole derivatives containing fluorine-substituted methylene groups.

Shibamoto et al. (1992) *Int. J. Radiation Biol.* 61:473–478, Sasai et al. (1991) *Int. J. Radiation Oncol. Biol. Phys.* 20:1249–1254 and Sasai et al. (1991) *Int. J. Radiation Oncol. Biol. Phys.* 21:1231–1234, describe KU-2285, a 2-nitroimidazole with a $N^1$-substituent of $CH_2CF_2C(O)$ $NHCH_2CH_2OH$.

Mashiba et al. (1991) *Life Sciences* 49:1419–1425 and Shibamoto et al. (1991) *Int. J. Radiation Biol.* 59:105–115 describe 1-(4'-hydroxy-2'-butenoxy)-methyl-2-nitroimidazole (RK-28).

Shibamoto et al. (1989) *Int. J. Radiation Oncol. Biol. Phys.* 16:1045–1048 describes 2-nitroimidazoles and 3-nitro-1,2,4-triazoles bearing one or two fluorine atoms on their side chains.

Murayama et al. (1989) *Int. J. Radiation Oncol. Biol. Phys.* 17:575–581 describes 1-[2-hydroxy-1-(hydroxymethyl)ethoxy]methyl-2-nitroimidazole (RP-170).

Li et al. (1991) *Cancer Comm.* 3:133–139 describe hexafluoromisonidazole (CCI-103F) as a hypoxic cell label that can be measured by in vivo [$^1$H]/[$^{19}$F] magnetic resonance spectroscopy.

SUMMARY OF THE INVENTION

It is accordingly a primary object of the invention to address the above-mentioned need in the art by providing novel compounds which are useful for detecting tumors and monitoring anti-tumor therapy using magnetic resonance imaging and/or magnetic resonance spectroscopy.

It is another object of the invention to provide pharmaceutical compositions for imaging hypoxic tumor cells and for monitoring the progress of anti-tumor therapy.

It is a further object of the invention to provide a method for the non-invasive imaging of hypoxic tumor cells and for monitoring the progress of anti-tumor therapy, comprising administering an effective amount of a compound of the invention to the individual undergoing treatment.

Additional objects, advantages and novel features of the invention will be set forth in part in the description which follows, and in part will become apparent to those skilled in the art upon examination of the following, or may be learned by practice of the invention.

In a first embodiment, the invention relates to certain novel compounds which are useful as tumor detecting agents using magnetic resonance imaging and magnetic resonance spectroscopy techniques. The novel compounds presently disclosed and claimed possess relatively low neurotoxic activity, i.e., do not accumulate to any appreciable degree in the brain, concentrate in tumor cells in a concentration sufficiently high to give a $^{19}$F signal of sufficient intensity for detection using MRI/MRS techniques and may be readily synthesized. The novel compounds have the structural formula (I)

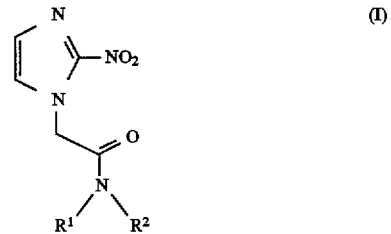

wherein $R^1$ and $R^2$ are independently selected from the group consisting of: hydrogen; a monosaccharide optionally functionalized to contain a lower alkoxy, lower acyl, amine, halogen or carboxylic acid moiety, wherein the linkage is to a carbon atom of the monosaccharide; lower alkyl substituted with a —$CF_3$ group and further substituted with at least one $R^3$, wherein $R^3$ is selected from the group consisting of —OH and —$NR^4_2$ in which $R^4$ is hydrogen or lower alkyl; and five- and six-membered heterocyclic rings containing one heteroatom selected from the group consisting of N, O and S, or wherein $R^1$ and $R^2$ are linked to form a five- or six-membered heterocyclic ring having at least one heteroatom selected from the group consisting of N and O, and wherein if the heteroatom is N, it may be unsubstituted or substituted with a lower alkyl group, or it may be in salt form associated with an anionic counterion such as a halide or oxalate, and further wherein the five- or six-membered heterocyclic ring is substituted with a —CF$_3$ moiety and optionally further substituted with —OH, —CH$_2$OH or —NH$_2$ on the same carbon atom as the —CF$_3$;

with the following provisos: that at least one of R$^1$ and R$^2$ is lower alkyl substituted with a —CF$_3$ group and further substituted with at least one R$^3$; and that if either R$^1$ or R$^2$ contains four or more carbon atoms it is substituted with more than one R$^3$ group.

The invention also relates to pharmaceutical compositions containing one or more of the above compounds in combination with a pharmaceutically acceptable carrier. These compositions will generally although not necessarily be administered orally.

The invention further encompasses methods for detecting hypoxic tumor cells by administering an effective tumor-detecting amount of a compound of the invention to the individual undergoing MRI or MRS evaluation. MRI and/or MRS is then used to detect any of the compound which is associated with and retained by tumor cells present in the individual.

BRIEF DESCRIPTION OF THE FIGURES

FIG. 6A is a magnetic resonance spectrum of SR 4554 and 5-fluorotryptophan, while

DETAILED DESCRIPTION OF THE INVENTION

Figure 1:
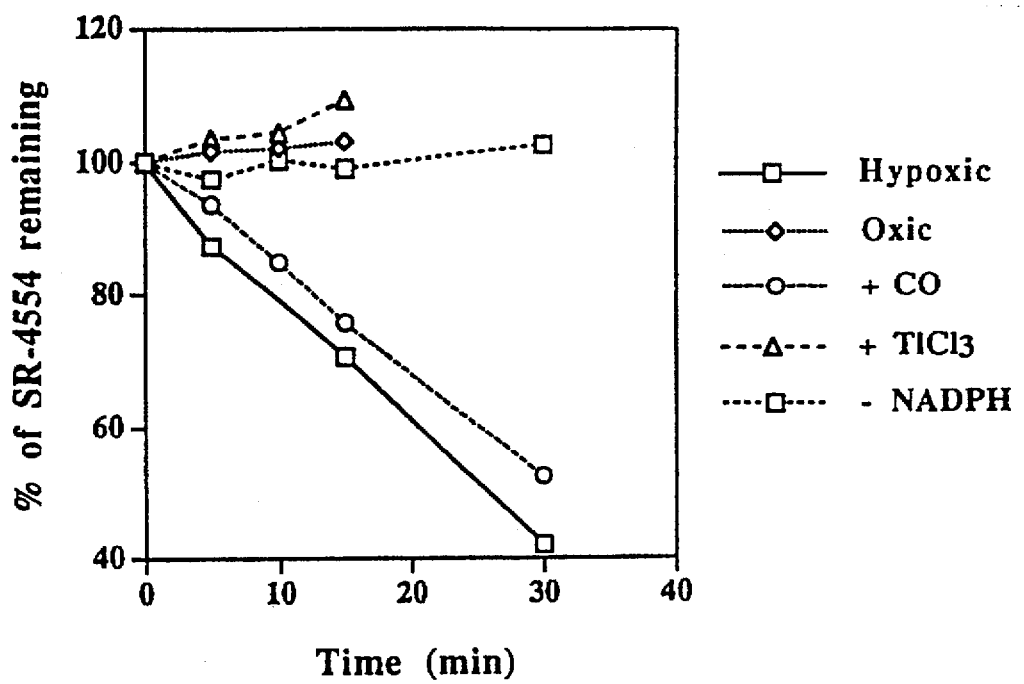
FIG. 1 illustrates in graph form the metabolism of SR 4554 by mouse liver microsomes, as explained in Example 4.

Definitions and Nomenclature:

Before the present compounds, compositions and methods are disclosed and described, it is to be understood that this invention is not limited to specific reagents or reaction conditions, specific pharmaceutical carriers, or particular administration regimens, as such may vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "a 2-nitroimidazole analog" includes mixtures of 2-nitroimidazole analogs, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 1 to 12 carbon atoms. The term "lower alkenyl" intends an alkenyl group of one to six carbon atoms, preferably one to four carbon atoms. The term "cycloalkenyl" intends a cyclic alkenyl group of three to eight, preferably five or six, carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "acyl" as used herein is used in its conventional sense to refer to an alkyl group bound through a —(CO)— linkage. The term "lower acyl" refers to an acyl group in which the alkyl group bound through the carbonyl linkage is a lower alkyl group.

"Halo" or "halogen" refers to fluoro, chloro, bromo or iodo, and usually relates to halo substitution for a hydrogen atom in an organic compound. Of the halos, chloro and fluoro are generally preferred.

The term "sugar moiety" is intended to encompass monosaccharides. The sugar moiety should be selected so that it enhances water solubility and/or decreases lipophilicity of the tumor detecting compound. The term "sugar" includes those moieties which have been modified, e.g., wherein one or more of the hydroxyl groups are replaced with halogen, alkoxy moieties, aliphatic groups, or are functionalized as ethers, amines, or the like. Examples of modified sugars include: those which contain a lower alkoxy group in place of a hydroxyl moiety, i.e., α- or β-glycosides such as methyl α-D-glucopyranoside, methyl β-D-glucopylamines, and the like; those which have been reacted with amines, i.e., N-glycosylamines or N-glycosides such as N-(α-D-glucopyranosyl)methylamine; those containing acylated hydroxyl groups, typically from 1 to 5 lower acyl groups; those containing one or more carboxylic acid groups, e.g., D-gluconic acid or the like; and those containing free amine groups such as D-glucosamine, D-galactosamine, N-acetyl-D-glucosamine or the like. Examples of preferred saccharides are glucose, galactose, fructose, ribose, mannose, arabinose, xylose, with D-glucose particularly preferred.

By the term "effective amount" of an agent as provided herein is meant a nontoxic but sufficient amount of the agent to provide the desired signal intensity such that MRI or MRS may be performed. As will be pointed out below, the exact amount required will vary from subject to subject, depending on the species, age, and general condition of the subject, the severity of the disease associated with presence of the tumor, the particular fluorinated 2-nitroimidazole analog and its mode of administration, and the like. Thus, it is not possible to specify an exact "effective amount". However, an appropriate effective amount may be determined by one of ordinary skill in the art using only routine experimentation The term "pharmaceutically acceptable" to describe pharmaceutical carriers and the like intends materials which are not biologically or otherwise undesirable, i.e., the material may be administered to an individual along with the selected fluorinated 2-nitroimidazole analog without causing any undesirable biological effects or interacting in a deleterious manner with any of the other components of the pharmaceutical composition in which it is contained.

"Optional" or "optionally" means that the subsequently described event or circumstance may or may not occur, and that the description includes instances where said event or circumstance occurs and instances where it does not. For example, the phrase "optionally functionalized monosaccharide" means that a monosaccharide moiety may or may not be functionalized and that the description includes both functionalized monosaccharides as well as monosaccharides which are not functionalized.

The invention is directed to novel fluorinated 2-nitroimidazole derivatives useful for the non-invasive detection of tumor hypoxia by magnetic resonance imaging and/or magnetic resonance spectroscopy. The 2-nitroimidazole class of compounds undergo nitroreduction to reactive intermediates which form covalent adducts with macromolecules. The binding of these compounds to tissues increases with decreasing oxygen concentration (or increasing hypoxia) and thus enables the compounds to act as markers for tumor hypoxia. The introduction of a $^{19}F$ label permits detection of the retained compounds using non-invasive techniques such as magnetic resonance imaging and magnetic resonance spectroscopy. Since solid tumors generally have regions of hypoxic cells that enable them to remain viable despite intensive treatments the detection and quantification of regions of hypoxia in tumors would enable a rational selection of patients most likely to benefit from hypoxia-targeted therapies, such as radiosensitizers, chemosensitizers and other bioreductively activated drugs. Additionally, observing the response of these cells will result in improved treatment procedures.

The Novel Compounds:

The novel compounds provided herein are those defined by the structural formula (I) wherein $R^1$ and $R^2$ are independently selected from the group consisting of: hydrogen; a monosaccharide optionally functionalized to contain a lower alkoxy, lower acyl, amine, halogen or carboxylic acid moiety, wherein the linkage is to a carbon atom of the monosaccharide; lower alkyl substituted with a —$CF_3$ group and further substituted with at least one $R^3$, wherein $R^3$ is selected from the group consisting of —OH and —$NR^4_2$ in which $R^4$ is hydrogen or lower alkyl; and five- and six-membered heterocyclic rings containing one heteroatom selected from the group consisting of N, O and S, or wherein $R^1$ and $R^2$ are linked to form a five- or six-membered alkyl ring substituted with a —$CF_3$ moiety;

with the following provisos: that at least one of $R^1$ and $R^2$ is lower alkyl substituted with a —$CF_3$ group and further substituted with at least one $R^3$; and that if either $R^1$ or $R^2$ contains four or more carbon atoms it is substituted with more than one $R^3$ group.

Examples of preferred compounds within this group are as follows:

those wherein $R^1$ is hydrogen and $R^2$ is lower alkyl substituted with a —$CF_3$ group and at least one $R^3$ groups, preferably two $R^3$ groups, and most preferably such compounds wherein $R^3$ is hydroxyl;

those wherein $R^1$ and $R^2$ are independently lower alkyl substituted with a —$CF_3$ group and at least one $R^3$, and preferably such compounds wherein $R^1$ and $R^2$ are nonidentical; and those wherein $R^1$ is a monosaccharide and $R^2$ is lower alkyl substituted with a —$CF_3$ group and at least one $R^3$, and preferably such compounds wherein $R^1$ is D-glucose.

Examples of particularly preferred compounds are wherein $R^1$ is 2-hydroxy-3,3,3-trifluoropropyl, $R^2$ is hydrogen, hydroxyethyl or D-glucose, and $R^3$ is —OH.

Specific compounds within the group are as follows:

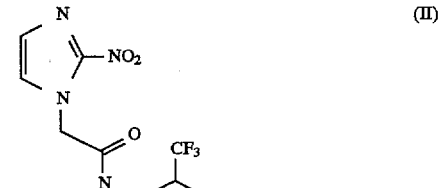

(II)

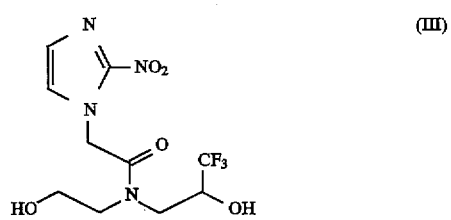

(III)

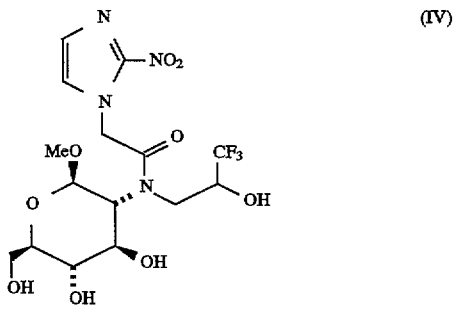

(IV)

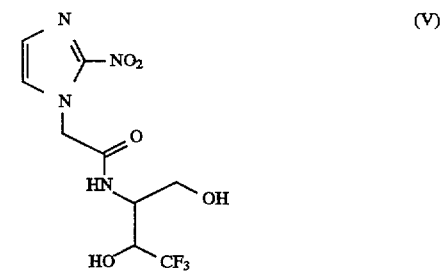

(V)

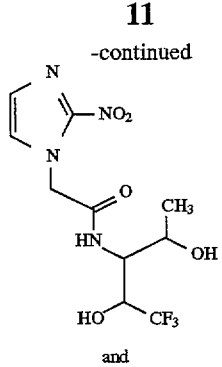

(VI)

and

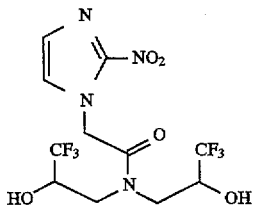

(VII)

Utility and Administration:

The compounds of the invention defined by structural formula (I), including the pharmacologically acceptable salts thereof, are useful as tumor detecting agents, more particularly as hypoxic cell-specific probes, and may be conveniently formulated into pharmaceutical compositions composed of one or more of the compounds in association with a pharmaceutically acceptable carrier. *Remington's Pharmaceutical Sciences,* 18th edition, by E. W. Martin (Mack Publ. Co., Easton Pa. 1990) discloses typical carriers and conventional methods of preparing pharmaceutical compositions which may be used to prepare formulations using the tumor detecting agents of the invention. The method of the invention involves administering an effective tumor-detecting amount of the selected compound to the individual undergoing evaluation, i.e., a mammalian individual, followed by detecting any of the compound which is associated with and retained by tumor cells that are present. Such detecting, as noted above, is conducted using non-invasive techniques such as magnetic resonance imaging or magnetic resonance spectroscopy.

The compounds may be administered orally, parenterally (e.g., intravenously), by intramuscular injection, or by intraperitoneal injection, or the like. Intravenous administration of a solution formulation is clinically preferred, as control over the exact dose given may be more readily achieved. The amount of active compound administered will, of course, be dependent on the subject undergoing evaluation, the subject's weight, the manner of administration and the judgment of the prescribing physician.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

For pulmonary administration, it is preferred that the drug to be administered be transformed into powder form, combined with a conventional propellant, e.g., a halohydrocarbon such as tetrafluoroethane, trichlorofluoromethane, dichlorofluoromethane, or the like, and administered as an aerosol formulation. The formulation preferably contains surfactants as well, to facilitate and stabilize the suspension or dispersion of drug powder in the propellant. The drug powder will normally constitute about 0.1 to 10 wt.% of the formulation. The solid particle aerosol formulation will typically be administered in one or more unit doses, with dosages as set out above, to provide therapeutic levels of drug.

Process for Preparation:

The aim of the invention is to produce fluorine containing 2-nitroimidazoles with the desired physicochemical properties that both decrease the neurotoxic side effects commonly found with nitroheterocycles and increase the accumulation of these drugs in hypoxic tumor cells. The major problems with the compounds utilized to date are their relatively weak signals due to the number of fluorine atoms per molecule (such as with 5-fluorouracil) or their neurotoxic side effects (CCI-103F and Ro 07-0741) which presumably relate to their high lipophilicities. Brown et al. (1980) *Radiation Res.* 82:171-190. The inventors herein have synthesized compounds containing the trifluoromethyl group, as the number of fluorine atoms per molecule of drug has been found to be important for high signal strength and sensitivity with MRI/MRS evaluation. The 2-nitroimidazole functionality is considered necessary since irreversible covalent binding of the labeled drug to macromolecules in hypoxic cells results in increased concentration of fluorine label in these cells, in turn contributing to improved detection of solid tumors.

The synthetic approach exemplified below is based on the synthesis of fluorinated analogues of the bioreductively activated nitroheterocyclic compound Etanidazole (SR 2508) previously developed at SRI by W. W. Lee and J. M. Brown (Stanford University) (Brown et al. (1981) *Int. J. Radiation Oncol. Biol. Phys.* 7:695-703) who showed that Etanidazole was less neurotoxic than Misonidazole, which correlated with lower lipophilicity (Misonidazole: log P=−0.32; Etanidazole: log P=−1.28).

The initial compound synthesized in this series, N-(2-hydroxy-3,3,3-trifluoropropyl)-2-(2-nitro-1H-imidazol-1-yl)acetamide (SR 4554), contained all the desired components for a suitable probe molecule but was found to be rather insoluble in 0.9% saline solution (Etanidazole=551 mmol ml$^{-1}$ vs SR 4554=23 mmol ml$^{-1}$) and had a much more positive logP than predicted (Etanidazole=−1.28 vs SR 4554=−0.20). While not wishing to be bound by thoery, it is the unusual electronic nature of the trifluoromethyl group which was assumed to be responsible for these phenomena. The scope of this class of fluorinated 2-nitroimidazoles was therefore expanded to include more aqueous soluble and hydrophilic derivatives.

Addition of the hydrophilic hydroxyethyl side chain to give the tertiary amido analogue SR 4557 was expected to overcome the effect of the trifluoromethyl group and give a compound with suitable physicochemical properties. Surprisingly, SR 4557 showed very little change in logP value (SR 4557=−0.36 vs SR 4554=−0.20), although solubility in 0.9% saline solution was greatly increased (SR 4557=628 mmol ml$^{-1}$ vs SR 4554=23 mmol ml$^{31\ 1}$). The lipophilic characteristics of SR 4554 and SR 4557 were originally considered to make these compounds unsuitable for use in vivo. However, the work described here with SR 4554 has shown that this assumption may be invalid for these types of fluorinated derivatives since pharmacokinetic studies show that while SR 4554 accumulates in hypoxic tumor cells in high enough concentration to give a $^{19}$F signal of sufficient intensity for MRI/MRS techniques, it does not accumulate to any appreciable degree in the brain.

The compounds of the invention may be prepared in high yield using relatively simple, straightforward methods as exemplified in the experimental section herein.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

Experimental

Extraction of Tissue Samples and Standards

Silver nitrate solution (25 µl; 30% w/v) was added to 250 µl of tissue samples and standards and to 20 µl of internal standard solution (12.5 µg/ml in 0.1M Tris buffer, pH 7.4). Samples were then vortexed and centrifuged (2000×g) for 5 min. The extracted samples 50 µl) were then injected into the HPLC.

HPLC Methodology

The chromatographic system consisted of a WISP Model 712 autosampler (Waters Chromatography Ltd.), Model 660 gradient controller with a quaternary HPLC pump, a Model 991 photodiode array detector and a NEC Powermate SX/16 personal computer running Waters 991 photodiode array software. A reversed phase chromatographic separation was performed on a 10 µm µ Bondapak C18 (3.9×300 mm) analytical column (Millipore) at ambient temperature. Pellicular ODS (Whatman) packed in a 2×6.5 mm stainless steel column (Upchurch Scientific, Inc.) was used as a pre-column. The mobile phase was methanol/H$_2$O) (15:85). All solvents were filtered through a 0.45 µm Teflon PTFE/polypropylene filter membrane, de-gassed with helium and delivered isocratically at a flow rate of 2 ml/min. The column effluent was monitored by UV-photodiode array detection at 324 nm (UV range=200 to 500 nm). The peak area ratio of analyte to internal standard was used for conversion of the detector response to concentration estimates via the construction of a calibration curve.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

All starting materials and reagents are commercially available.

EXAMPLE 1

This example describes preparation of N-(2-hydroxy-3,3,3-trifluoropropyl)-2-(2-nitro-1H-imidazol-1-yl)acetamide (SR 4554).

The synthesis of SR 4554 is shown in Scheme 1. Conversion of 2-nitroimidazole (4) into its sodium salt was accomplished by treatment with sodium methoxide in methanol-DMF at 150° C. for 10 min. Subsequent reaction with methyl bromoacetate in DMF at 85° C. for 20 min gave the methyl ester (5). This compound was then converted into the carboxylic acid (6) by treatment of 5 with 0.1 N NaOH at 100° C. for 15 min followed by acidification with 1M HCl. The fluorine labelled side chain was prepared by reaction of trifluoroacetaldehyde hemiacetal (7) and nitromethane in the presence of potassium carbonate at 60° C. for 3 h. Pure nitro-compound (8) was obtained from the reaction mixture by distillation at 115° C. at 60 mmHg. Reduction of the nitro group of 8 was accomplished by hydrogenation at 40 psi with Raney-nickel catalysis, treatment of the filtered reaction mixture with ethereal HCl at −20° C. gave the amino-compound (9) as its HCl salt. Coupling of the carboxylic acid (6) with this amino-compound was carried out by first converting the acid group of 6 to the mixed anhydride using iso-butylchloroformate and N-methylmorpholine in tetrahydrofuran (THF) at 0° C. Addition of the amine (9) and a further equivalent of N-methylmorpholine resulted in the formation of SR 4554, which was purified by column chromatography and recrystallization from ethyl acetatehexanes.

SCHEME 1

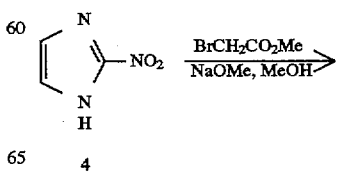

4

SCHEME 1 -continued

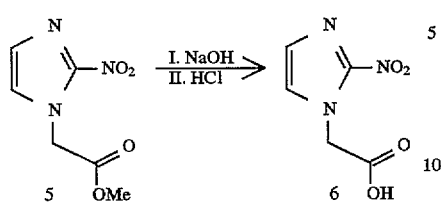

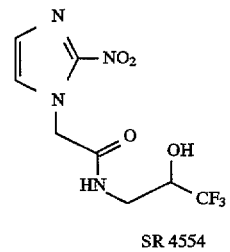

SR 4554

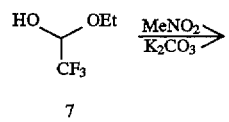

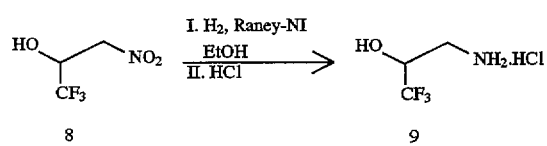

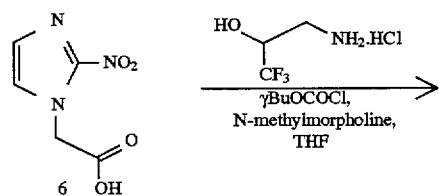

EXAMPLE 2

This example describes preparation of N-(2-hydroxyethyl)-N-(2-hydroxy-3,3,3-trifluoropropyl)-2-(2-nitro 1H-imidazol-1-yl)acetamide (SR 4557).

The synthesis of SR 4557 is shown in Scheme 2. Reduction of 1-bromo-3,3,3-trifluoroacetone (10) with lithium aluminum hydride in refluxing ether gave the bromo-alcohol (11) which was purified by distillation at 120°–122° C. This compound was cyclized using NaOH at 100° C. to the epoxide (12) which distilled directly from the reaction mixture. Reaction of the epoxide (12) with ethanolamine in H₂O gave the diol (13) which was purified by distillation at 105°–115° C. at 0.05 mmHg. Coupling of this intermediate with the carboxylic acid (6) was carried out using the same procedure for SR 4554. Purification by column chromatography gave SR 4557 as an amorphous solid.

SCHEME 2

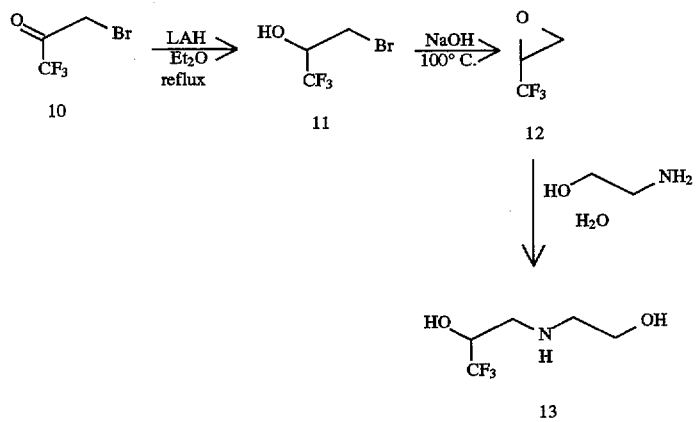

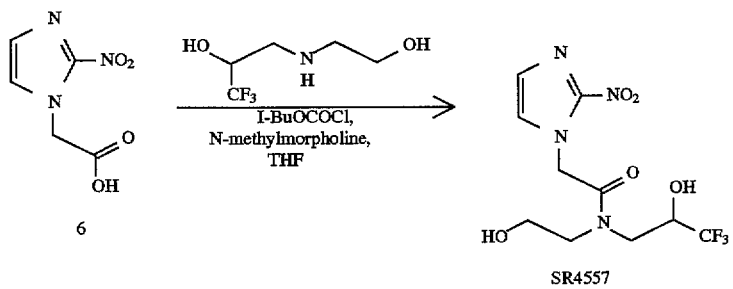

SR4557

EXAMPLE 3

This example describes preparation of methyl 2-deoxy-2-[N-2-hydroxy-3,3,3-trifluoropropyl-2-(2-nitro-1H-imidazol-1-yl)acetamido-β-D-glucopyranoside The synthetic approach used for the D-glucose derivative (1) is shown in Scheme 3. Treatment of D-glucosamine hydrochloride (14) with benzyloxychloroformate in aqueous sodium bicarbonate gave (15) which was converted into the methyl glycoside (16) by refluxing in methanol containing hydrochloric acid. Compound (6) was then converted to the triacetoxy derivative (17) by treatment with acetic anhydride in pyridine. Removal of the benzyloxy carbamate group was accomplished using $H_2$ and 10% palladium-on-carbon in ethanol to give the amino compound (18). Treatment of (18) with the trifluoromethyl epoxide (12) in acetonitrile at a temperature of 85° C. in a sealed-tube resulted in the alkylation of its primary amino-group to give (19). Coupling of the amino compound (19) with 2-(2'-nitro-imidazole) acetic acid (6) using iso-butylchloroformate and N-methylmorpholine in THF as described above and removal of the acetoxy protecting groups with catalytic sodium methoxide in methanol gave the product (1) as a crystalline solid which was a mixture of diastereoisomers.

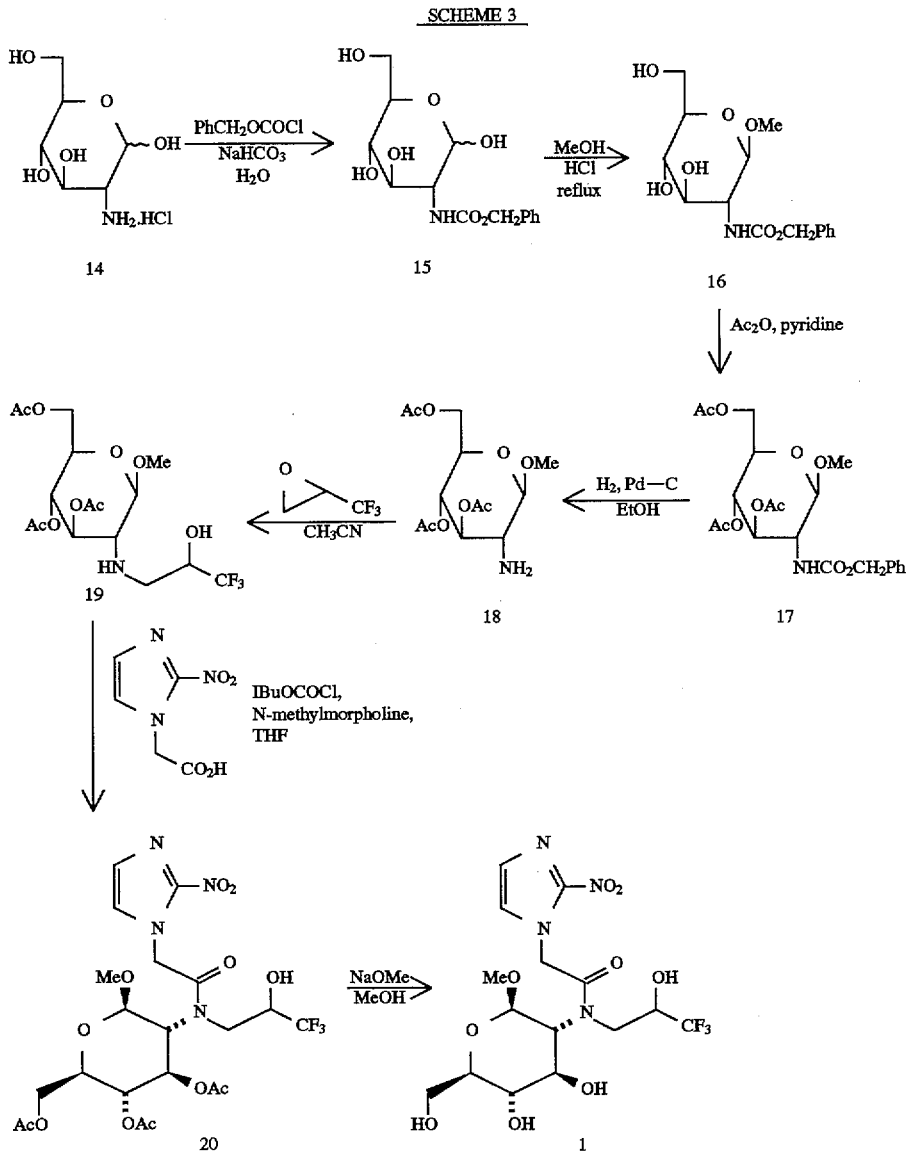

SCHEME 3

EXAMPLE 4

Metabolism of SR 4554 In Vitro

SR 4554 was reduced by mouse liver microsomes as well as purified rat and human cytochrome P450 reductase under hypoxia (100% nitrogen). Reduction was completely inhibited by air and also in the presence of an inhibitor of cytochrome P450 reductase ($TiCl_3.4H_2O$; 0.2 mg/ml). In contrast, carbon monoxide only caused a 15% inhibition of metabolism in microsomes. Kinetics of the microsomal metabolism of the drug were characterized by a $K_m$ and $V_{max}$ of 650 μM and 16.84 nmol $min^{-1}$ $mg^{-1}$, respectively. This suggests the involvement of cytochrome P450 reductase in the initial steps of bioactivation.

The characteristics of reductive metabolism of SR 4554 by mouse liver microsomes (0.5 mg/ml protein) are depicted in FIG. 1. Samples were removed at various time points, extracted with silver nitrate and analyzed by high performance liquid chromatography (HPLC) as described above. SR 4554 was metabolized under hypoxic conditions as shown by parent drug loss. The reaction was completely inhibited in the absence of cofactor (NADPH) and when carried out in air. The cytochrome P450 inhibitor—carbon monoxide—inhibited the hypoxic metabolism of SR 4554 by 15%. In addition, the cytochrome P450 reductase inhibitor $TlCl_3.4H_2O$ (0.2 mg/ml) completely inhibited the reductive process. No other nitro-containing species were observed upon metabolism.

EXAMPLE 5

Retention of SR 4554 in Human Ovaian A2780 Spheroids Using Electron Energy Loss Spectroscopy About 100 spheroids (0.5–1 mm diameter) were incubated in a culture medium containing 1 mM SR 4554 for 3 hours. The spheroids were then washed with non-drug containing medium to remove unbound drug and 'chased' for a further 22 hours at 37° C. Samples were plunge frozen in liquid propane/isopentane at −185° C. for cryosectioning. Sections were analyzed by electron energy loss spectroscopy (EELS). SR 4554 was found to accumulate in the inner, more hypoxic cells near the center of the spheroids in preference to the outer cells, i.e., at the periphery.

Figure 2:
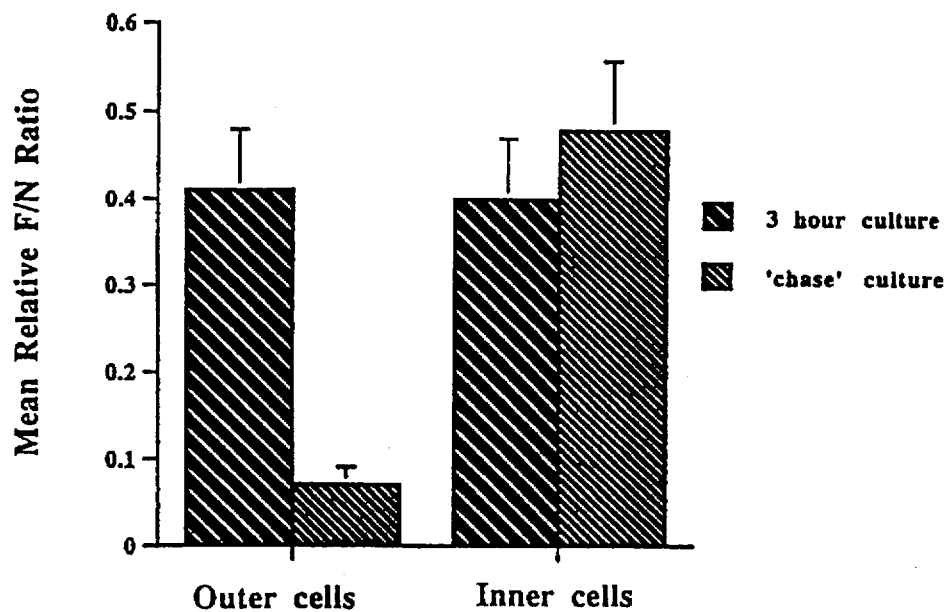
FIG. 2 presents in graph form evaluation of fluorine images of outer and inner cells of A2780 spheroids before and after chase culture obtained using electron energy loss spectroscopy (EELS), as described in Example 5.

Fluorine images of SR 4554 localization were obtained using EELS and quantified as fluorine/nitrogen (F/N) ratio as depicted in FIG. 2. Cells near the center of the spheroids were found to contain a significant seven-fold higher level of fluorine than cells at the periphery of the spheroid (p<0.05). These experiments were carried out in air.

EXAMPLE 6

Pharmacokinetics of SR 4554

EMT-6 tumor-bearing mice were used in this study. Mice were given a single intraperitoneal or intravenous injection (180 mg/kg body weight) or a single oral dose (p.o. 90 mg/kg) by lavage of SR 4554. Three mice were sacrificed per time point and blood obtained by cardiac puncture. The blood obtained was centrifuged to give plasma. Tumors, livers and brain were also obtained at various time points. Samples were extracted with silver nitrate and analyzed by high performance liquid chromatography (HPLC) using the procedures described in Example 4.

The absorption and clearance of SR 4554 in mice were found to be similar to that of low dose Misonidazole, with the drug showing very high oral (p.o.), i.v. and i.p. bioavailability (ratios relative to i.v. being: i.v., 100%; i.p., 100.4%1; p.o., 95.5%). This suggests that the drug could be effectively administered by any of these routes. Brown et al. (1980), supra; Workman et al. (1981) *Cancer Chemother. Pharmacol.* 6:39–49. Importantly, brain levels of SR 4554 as well as the brain/plasma ratio were generally low. In fact, unexpectedly, these were lower than levels previously quoted for most lipophilic 2-nitroimidazoles including Misonidazole and compares rather well with that of more hydrophilic nitroimidazoles like Etanidazole. Brown et al. (1980), supra; Workman et al. (1981), supra. It has been observed that brain concentrations of nitroimidazoles is governed by lipophilicity and relates the toxicity of the compounds. Brown et al. (1980), supra; Workman et al. (1981), supra. This observation suggests that lipophilicity is not the only criteria that governs the penetration of such compounds into the brain and that SR 4554 will be potentially less toxic than can be predicted from its lipophilicity.

Figure 3:
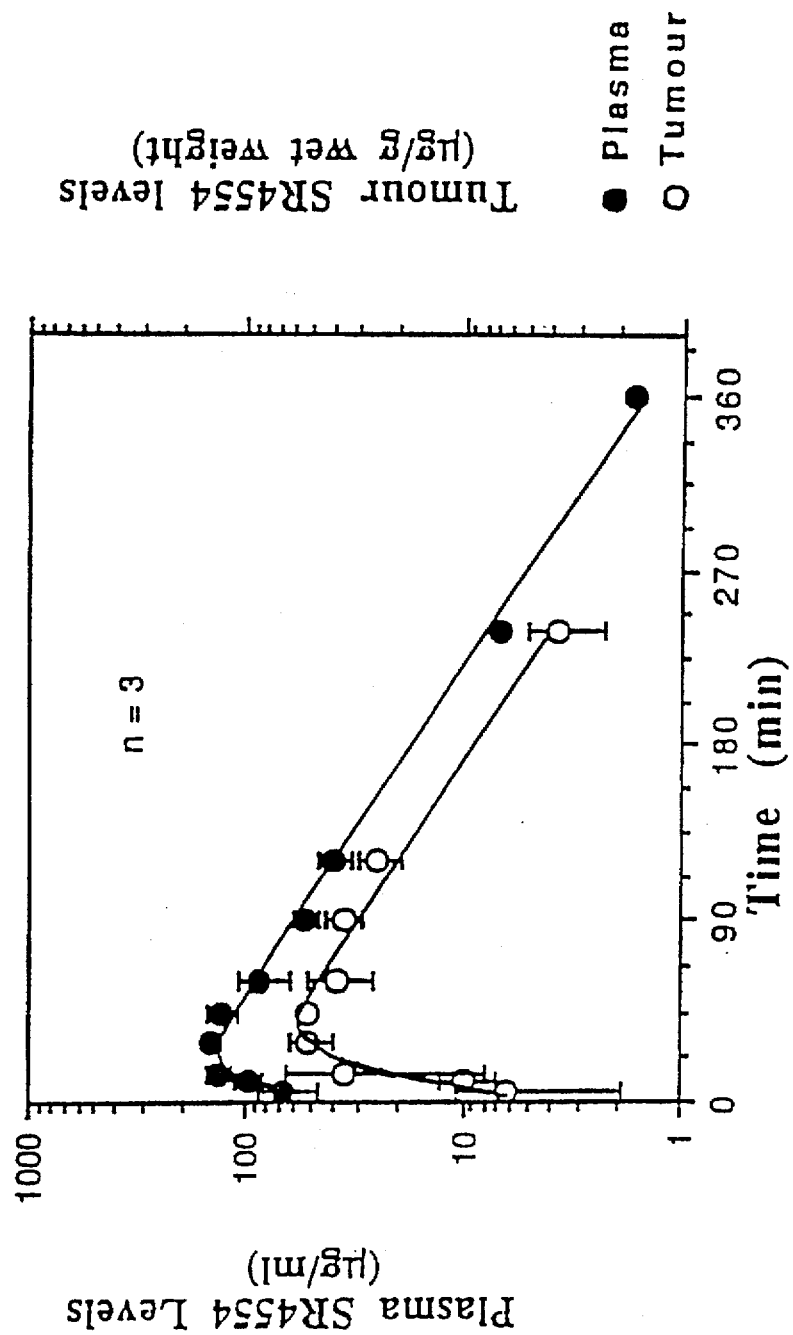
FIG. 3 depicts in graph form the pharmacokinetics of SR 4554 in EMT-6 tumor-bearing Balb/c mice, as evaluated in Example 6.

As depicted in FIG. 3, SR 4554 could be detected in plasma (limit of detection=25 ng/ml) at this dose level at least up until 6 hours postinjection. Tissue levels of drug were however below the limit of detection (100 ng/g tissue) at 6 hours. The peak SR 4554 concentration ($C_{max}$) was found to be 145 µg/ml and occurred ($t_{max}$) at 30 min. Tumor drug levels followed that of plasma with a $C_{max}$ of 52 µg/g and a $t_{max}$ of 45 min. Both plasma and tumor pharmacokinetics fitted a mono-exponential open model with model independent (trapezoidal) AUC values of 13.9 µg.ml$^{-1}$.min and 6.3 µg.ml$^{-1}$.min respectively. The corresponding model dependent AUC values were 15.1 and 7.7 µg.ml$^{-1}$.min, respectively. The elimination rate constants, a, were found to be 0.136 and 0.135 min$^{-1}$ (half life, $t_{1/2}$=50.8±1.6 min and 51.5±4.4) in plasma and tumor, respectively.

Table 1 shows the urinary excretion of SR 4554 in non-tumor-bearing female Balb/c mice. Interestingly, it was found that up to 66% of SR 4554 was detected as unchanged parent compound. These data is, in fact, more representative of hydrophilic than lipophilic compounds.

TABLE 1

| Urinary Excretion of SR 4554 in Non-tumor-bearing Balb/c Mice. | | |
| --- | --- | --- |
| Amount of Drug Injected (mg) | Amount of Drug Excreted (mg) | Fraction of Dose Excreted (%) |
| 3.55 | 2.62 | 73.80 |
| 3.34 | 2.39 | 71.56 |
| 3.48 | 1.83 | 52.59 |

Figure 4:
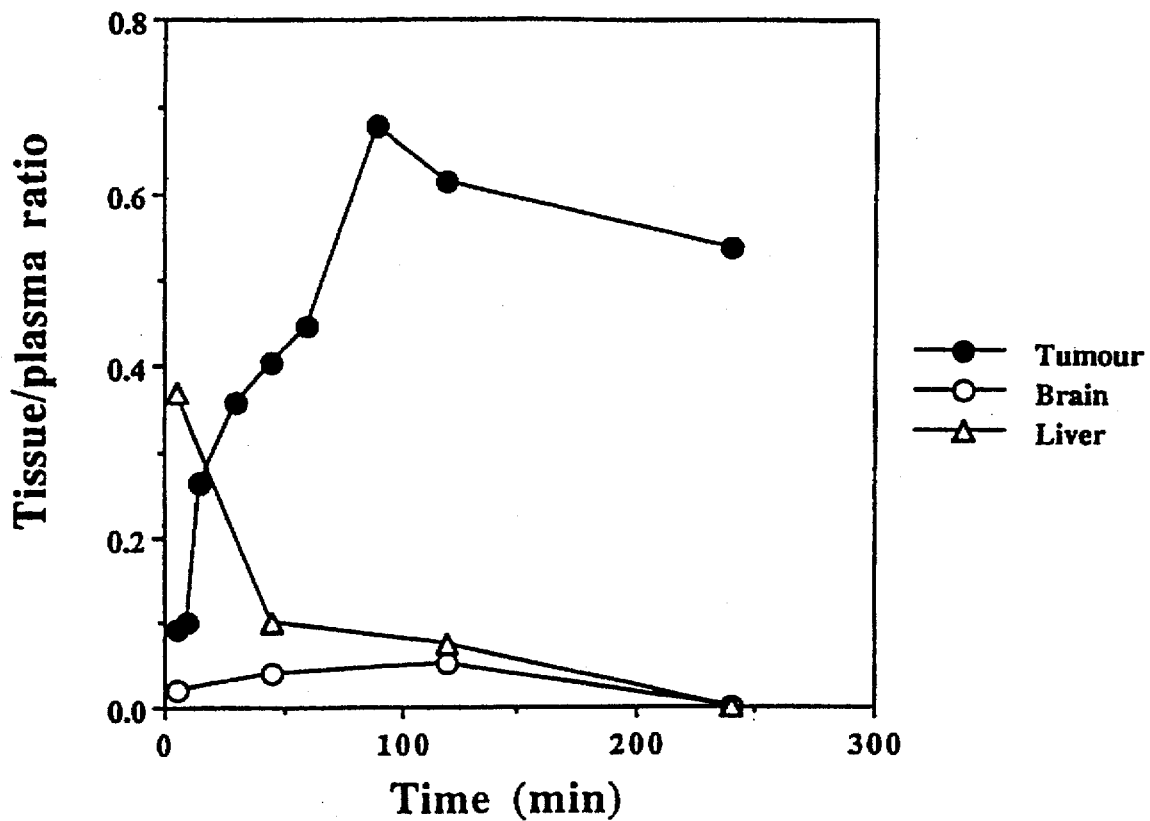
FIG. 4 depicts in graph form the tissue-to-plasma ratios of SR 4554 as a function of time following intraperitoneal injection, as described in Example 6.

The tissue-to-plasma ratios of SR 4554 as a function of time following intraperitoneal administration are illustrated in FIG. 4. The liver/plasma ratio decreased very rapidly while the brain/plasma ratios generally remained low throughout the observation period. At 240 min, the liver/plasma and brain/plasma ratios were about the same. Tumor/plasma ratio rose rapidly with a peak at about 90 min and decreased slowly with time. Following absorption Tumor/plasma ratio remained about 6 to 7 times more than liver/plasma and brain/plasma ratios.

EXAMPLE 7

Toxicity of SR 4554

Toxicity studies of SR 4554 were done in female Balb/c mice. Mice were injected with SR 4554 i.v with 191 mg/kg (0.05 ml/kg) body weight or i.p. with 383 mg/kg (0.05 ml/kg) body weight. Control mice were injected with an equivalent volume of solvent (saline).

Figure 5A:
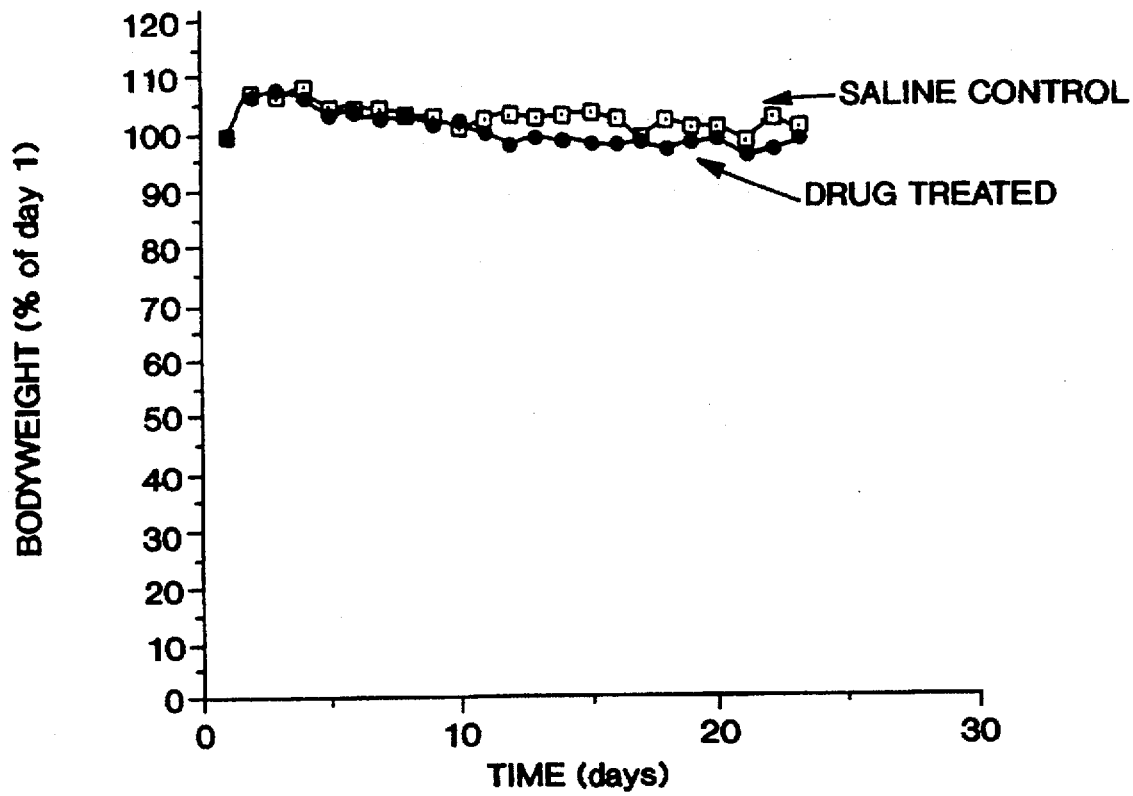
FIG. 5A illustrates in graph form the bodyweight of Balb/c mice after intravenous injection with SR 4554 or saline.
Figure 5B:
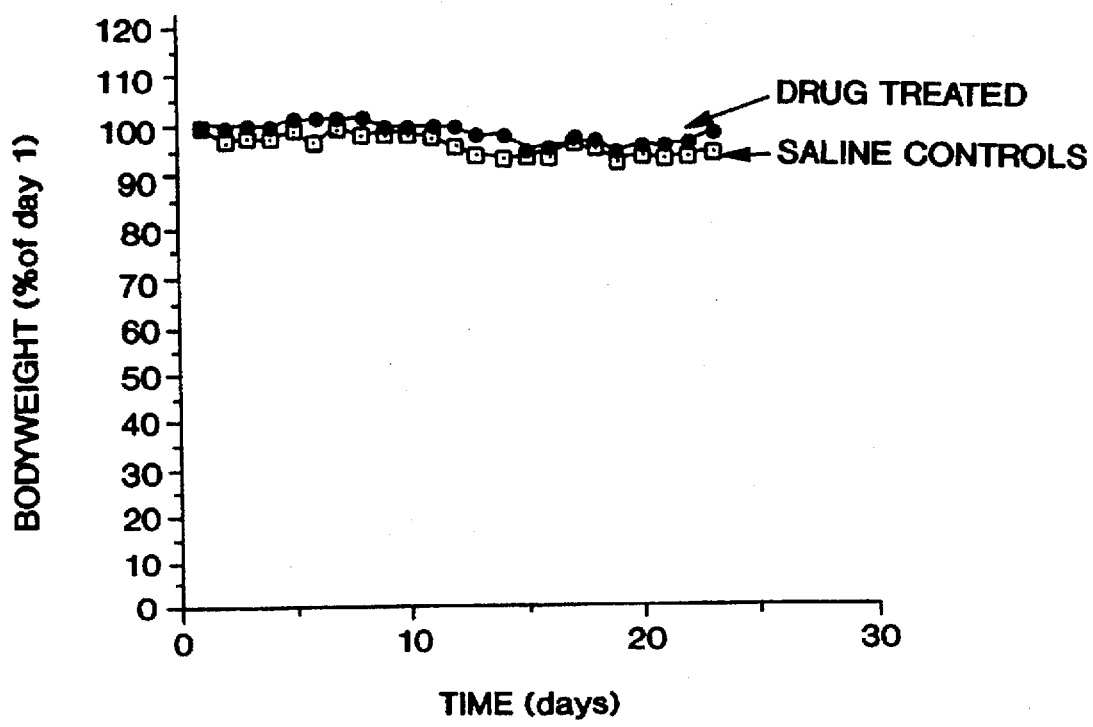
FIG. 5B depicts in graph form the bodyweight of Balb/c mice after intraperitoneal injection with SR 4554 or saline.

The average bodyweight of the mice (as a percentage of their weight on day 1 is charted in FIG. 5A for the i.v.-injected mice and FIG. 5B for the i.p.-injected mice. No differences were observed in bodyweight changes between treated and control mice. In addition, no behavioral changes or deaths were observed in either treated or control mice.

EXAMPLE 8

Magnetic Resonance Spectroscopy

SR 4554 was administered as a single intraperitoneal injection of 180 mg/kg to RIF-1 tumor-bearing female C₃H/He mice and EMT-6 tumor-bearing female Balb/c mice. In some experiments, hydralazine (5 mg/ml i.v.) was administered 1 h prior to the administration of SR 4554. Magnetic resonance spectroscopy (MRS) was conducted on a 4.7 Tesla (SISCO) nuclear magnetic resonance (NMR) spectrometer using a double-tuned ($^{19}F/^2H$) circuit at 45 min and 6 hr post injection of SR 4554. Drug concentrations were obtained using a modification of the method of Thulborn et al. (1983) *J. Magn. Reson.* 55:357–371. Specifically, the $^{19}F$ signal intensity was related to the natural abundance $^2H$ signal from tissue water. Calibrations involved the use of a reference bulb containing 5-fluorotryptophan (5-FTP) and acetic acid-d (AcOH-d). Tumors were excised immediately after MRS examination and original drug levels determined by high performance liquid chromatography (HPLC), as described in Example 6.

Figure 6A:
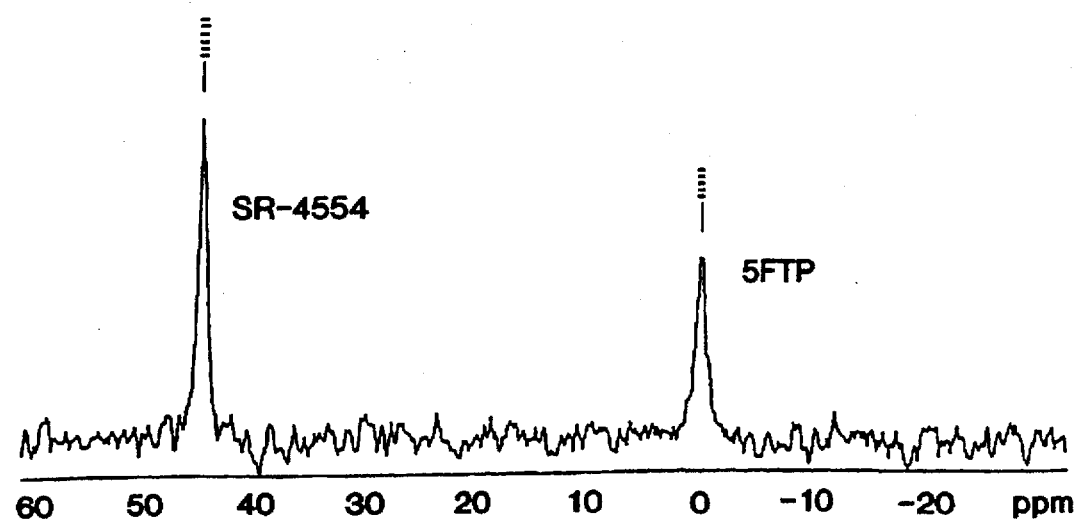
Figure 6B:
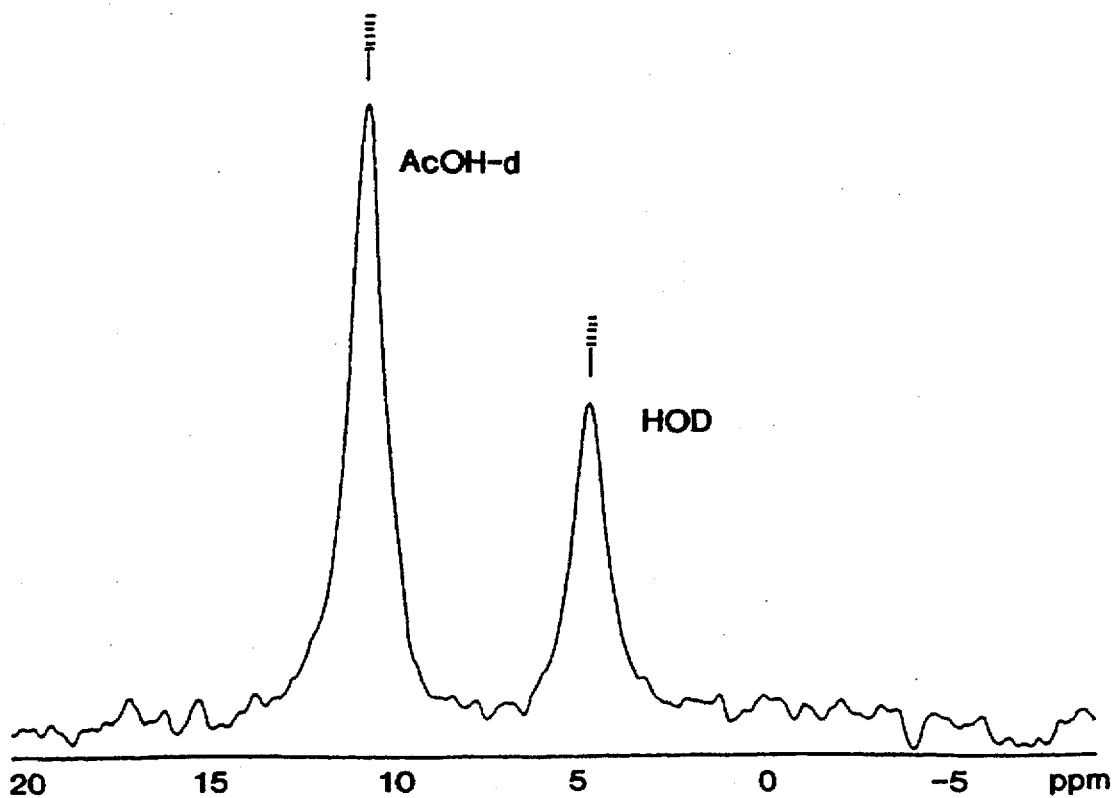
FIG. 6B is a magnetic resonance spectrum of HOD (naturally abundant deuterated water) and acetic acid-d.

Typical fluorine and deuterium spectra obtained from a RIF-1 tumor using MRS are depicted in FIG. 6. The SR 4554 peak is separated from that of 5-FTP by 45 ppm, while the HOD peak is separated from that of AcOH-d by 6 ppm. The SR 4554 peak is comprised of both original drug and related nitro-reduced metabolites.

In Table 2, shows $^{19}F$ signal levels corresponding to original drug and drug related metabolites (MRS) and original drug levels (HPLC) in RIF-1 tumors. Brain level MRS is also provided in Table 2. It is assumed that the retention of high concentrations of $^{19}F$ at 6 hr, despite the much lower (20 fold) concentration of original drug detected by HPLC at 7 hrs, represent one or more nitro-reduced metabolites. These results indicate that SR 4554 is rapidly cleared from the brain but selectively retained in tumors.

TABLE 2

Retention of SR 4554 in Mouse Tissues

| 45 min (MRS) | 6 hrs (MRS) | 7 hrs (HPLC) |
|---|---|---|
| Tumor (RIF-1) Drug Levels (µmol/g tissue) | | |
| 0.432 | 0.129 | 0.009 |
| 0.800 | 0.298 | 0.008 |
| 0.349 | 0.192 | 0.007 |
| 0.531 | 0.225 | ND¹ |
| Brain Drug Levels (µmol/g tissue) | | |
| 0.284 | ND | |
| 0.232 | ND | |
| 0.191 | ND | |
| 0.405 | ND | |

¹ND = Not Determined

Figure 7:
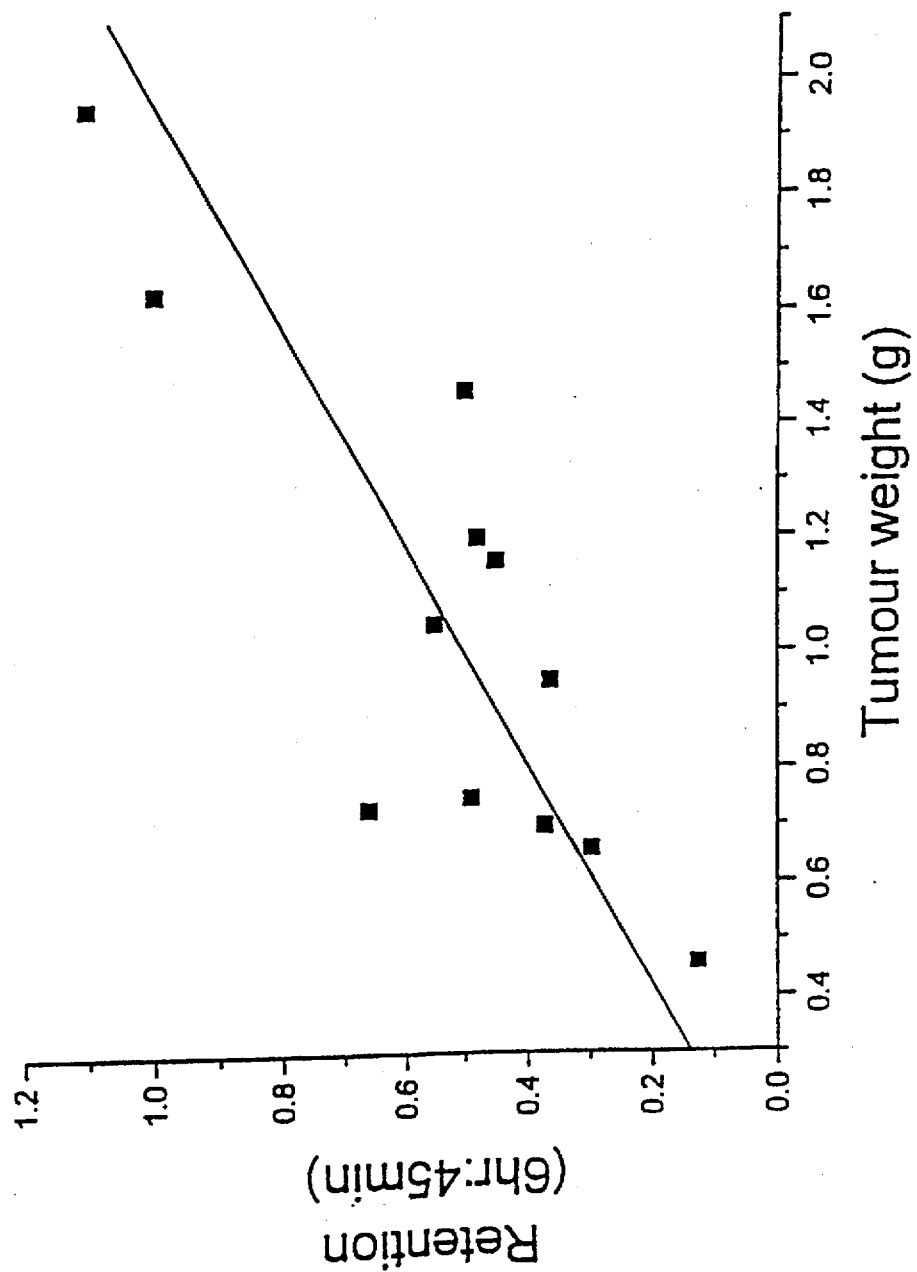
FIG. 7 depicts in graph form the retention of drug retained by RIF-1 tumors as a function of tumor weight, as described in Example 8.

The retention of drug signal in RIF-1 tumors is plotted as a function of tumor weight in FIG. 7. Tumor $^{19}F$ signal levels at 6 hrs and 45 min were calculated in µmol/g tumor. The retention of $^{19}F$ at 6 hrs relative to 45 min in the same tumors was compared to corresponding tumor weights in grams. In this tumor model (a low hypoxic fraction tumor) the relative retention (6 hrs/45 min) correlated with tumor weight (corr. coeff.=0.83).

Table 3 presents the results of a comparison between two tumor models. RIF-1 and EMT-6 tumors have a low and a high radiobiological hypoxic fraction, respectively. Moulder et al. (1984), supra. As expected, the retention of SR 4554 was greater in EMT-6 tumors than in RIF-1 tumors. In addition, these data also show that pre-treatment of mice with hydralazine produced a two-fold increase in retention.

TABLE 3

Retention of SR 4554 in Mouse Tumors

| Tumor Type | Retention¹ |
|---|---|
| RIF-1 | 0.53 ± 0.27 (n = 13) |
| RIF-1 (+ hydralazine) | 1.27 ± 0.50 (n = 6) |
| EMT-6 | 1.04 ± 0.66 (n = 12) |

¹Data represent mean retention of SR 4554 ± S.D. The number of mice used in each study is indicated in parenthesis. Tumor weight: 0.5 to 2.7 g.

Figure 8:
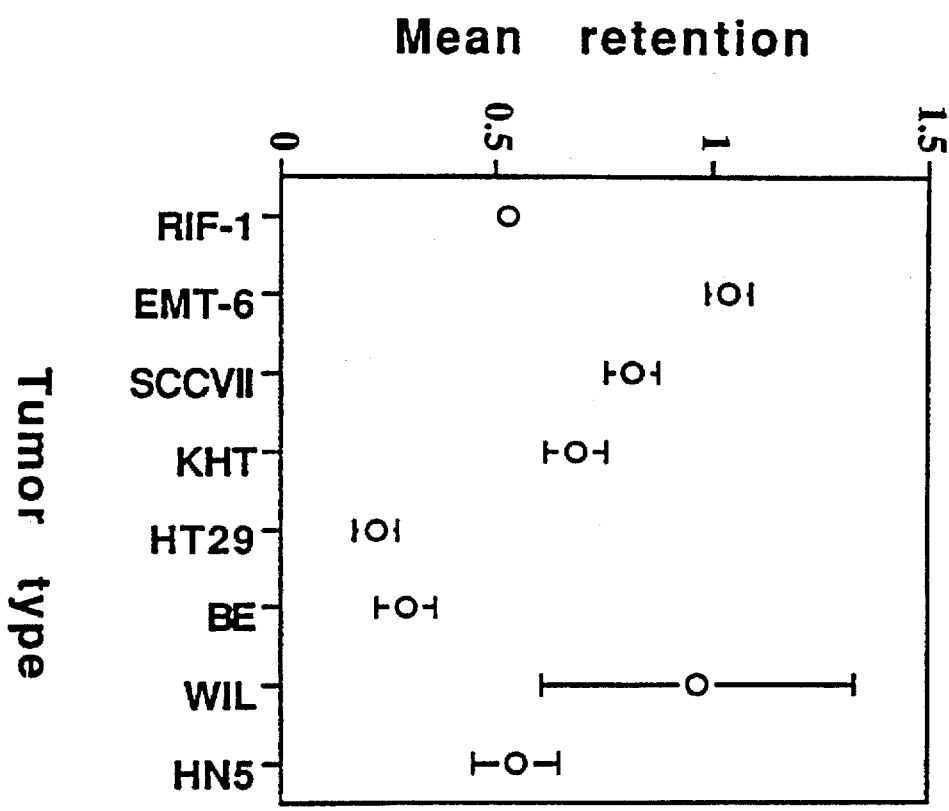
FIG. 8 depicts the retention of SR 4554 in murine and human tumor xenografts.

In addition to the above experiment, more extensive in vivo experiments have been performed. In order to assess the oxygenation status of various murine and human tumor xenografts, the retention of $^{19}F$ signal as measured by MRS was evaluated following SR 4554 administration. The data shown in FIG. 8 represent the mean ±SD of the ratios of $^{19}F$ retention (µmol/g) at 6 hrs relative to 45 mins. RIF1 (fibrosarcoma), EMT6 (squamous cell carcinoma) and KHT (adenocarcinoma) are murine tumors whereas HT29 (colon carcinoma), BB (colon carcinoma), WIL (non-small cell lung carcinoma) and HN5 (squamous cell carcinoma of the head and neck) are human tumor xenografts. Importantly, the data illustrates the varying degree of retention of SR 4554 by the different tumors. Apart from the WIL tumor, the retention of the drug in human tumor xenografts were lower than for the murine tumors. Generally, there was a trend, in which tumors which are known to have a greater hypoxic fraction retained more SR 4554.

Table 4 presents the influence of high levels of oxygen (carbogen breathing) on SR 4554 retention within the C3H mouse mammary tumor.

TABLE 4

Effect of Carbogen Breathing on SR 4554 Retention

| Mouse breathing | Retention |
|---|---|
| Air (20% O₂) | 0.62 +/− 0.17 |
| Carbogen (95% O₂) | 0.11 +/− 0.05 |

There was a significant (P<0.01) reduction in retention of SR 4554 between C3H tumors in mice breathing air compared to those breathing carbogen. This is consistent with improved oxygen levels in C3H tumors in mice as a response to carbogen breathing.

Tumor oxygenation measurements were performed 3 hours after SR 4554 administration using a polarographic needle oxygen electrode.

TABLE 5

Oxygen Electrode Measurement of SR 4554 Retention in C3H and SCVVII Tumors

| Tumor | SR 4554 Retention* | Median pO₂ |
|---|---|---|
| C3H-mammary | 0.79 +/− 0.36 | 4.6 +/− 2.4 |
| SCCVII | 0.57 +/− 0.14 | 1.7 +/− 0.8 |

*Data represents the mean retention of SR 4554 ± SD

The data in Table 5 suggest that there is no significant differences in SR 4554 retention or median pO₂ levels between these two tumors, although the conclusion is limited due to the relatively few mice studied. When SR 4554 retention was greater than 0.5, then the median pO₂ was less than 2 mm Hg, and 60% of the pO₂ values were less than 5 mm Hg, leading to the conclusion that subsequent retention

We claim:

1. A compound having the structural formula (I)

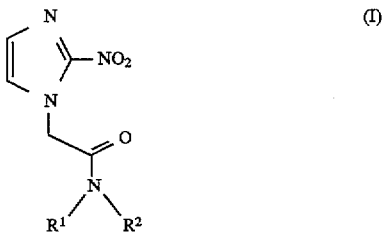

wherein:
R¹ and R² are independently selected from the group consisting of:
(a) hydrogen;
(b) an unsubstituted monosaccharide;
(c) a monosaccharide substituted with a lower alkoxy, lower acyl, amine, halogen or carboxylic acid moiety;
(c) lower alkyl substituted with a —$CF_3$ group and further substituted with one or two $R^3$ groups, wherein $R^3$ is selected from the group consisting of —OH and —$NR^4_2$ in which $R^4$ is hydrogen or lower alkyl; and
(d) five- and six-membered heterocyclic rings containing one heteroatom selected from the group consisting of N, O and S;
or wherein:
(e) R¹ and R² are linked to form a five- or six-membered heterocyclic ring containing a heteroatom selected from the group consisting of N and O, and further wherein the heterocyclic ring is either (i) substituted with one or two —$CF_3$ moieties, or (ii) substituted with one or two —$CF_3$ moieties and an additional substituent selected from the group consisting of —OH, —$CH_2OH$ and —$NH_2$, wherein the additional substituent is present on the same carbon atom as the —$CF_3$,
and wherein when one of R¹ and R² is a nitrogen-containing heterocyclic ring, or when R¹ and R² together form a nitrogen-containing heterocyclic ring, the nitrogen atom or atoms in the heterocyclic ring are either unsubstituted or substituted with a lower alkyl group,
with the following provisos: (i) that at least one of R¹ and R² is lower alkyl substituted with a —$CF_3$ group and further substituted with one or two $R^3$ groups; and (ii) that if either R¹ or R² contains four or more carbon atoms it is substituted with more than one $R^3$ group.

2. The compound of claim 1, wherein R¹ is selected from the group consisting of methyl α-D-glucopyranoside, methyl β-D-glucopyranoside, N-glycosylamines, N-glycosides, D-gluconic acid, D-glucosamine, D-galactosamine, N-acetyl-D-glucosamine.

3. The compound of claim 1, wherein R¹ is selected from the group consisting of glucose, galactose, fructose, ribose, mannose, arabinose and xylose.

4. The compound of claim 3, wherein R¹ is D-glucose.

5. A compound having the structural formula (I)

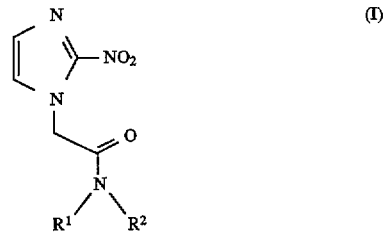

wherein:
R¹ and R² are independently selected from the group consisting of:
(a) hydrogen; and
(b) lower alkyl substituted with a —$CF_3$ group and further substituted with one or two $R^3$ groups, wherein $R^3$ is selected from the group consisting of —OH and —$NR^4_2$ in which $R^4$ is hydrogen or lower alkyl,
with the following provisos: (i) that at least one of R¹ and R² is lower alkyl substituted with a —$CF_3$ group and further substituted with one or two $R^3$ groups; and (ii) that if either R¹ or R² contains four or more carbon atoms it is substituted with two $R^3$ groups.

6. The compound of claim 5, wherein R¹ is hydrogen and R² is lower alkyl substituted with a —$CF_3$ group and one or two $R^3$ groups.

7. The compound of claim 6, wherein R² is substituted with one $R^3$ group.

8. The compound of claim 6, wherein R² is substituted with two $R^3$ groups.

9. The compound of claim 6, wherein $R^3$ is —OH.

10. The compound of claim 7, wherein $R^3$ is —OH.

11. The compound of claim 8, wherein $R^3$ is —OH.

12. The compound of claim 5, wherein R¹ and R² are independently lower alkyl substituted with a —$CF_3$ group and one or two $R^3$ groups.

13. The compound of claim 12, wherein R¹ and R² are the same.

14. The compound of claim 12, wherein R¹ and R² are different.

15. The compound of claim 12, wherein R¹ is substituted with one $R^3$ group.

16. The compound of claim 12, wherein R¹ is substituted with two $R^3$ groups.

17. The compound of claim 15, wherein R² is substituted with one $R^3$ group.

18. The compound of claim 15, wherein R² is substituted with two $R^3$ groups.

19. The compound of claim 16, wherein R² is substituted with one $R^3$ group.

20. The compound of claim 16, wherein R² is substituted with two $R^3$ groups.

21. The compound of claim 13, wherein R¹ and R² are each substituted with one $R^3$ group.

22. The compound of claim 13, wherein R¹ and R² are each substituted with two $R^3$ groups.

23. The compound of any one of claims 12, 13, 14, 15, 16, 17, 18, 19, 20, 21 and 22, wherein $R^3$ is —OH.

24. A compound having the structural formula (II)

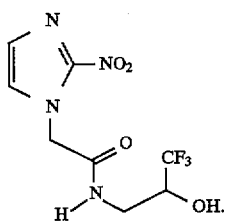

25. A compound having the structural formula (III)

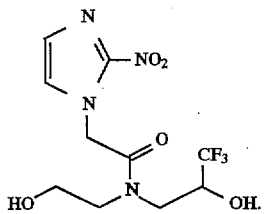

26. A compound having the structural formula (IV)

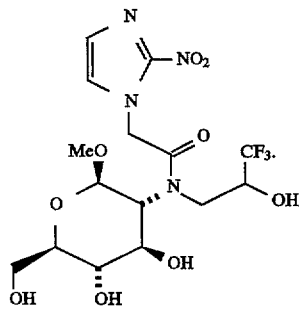

27. A compound having the structural formula (V)

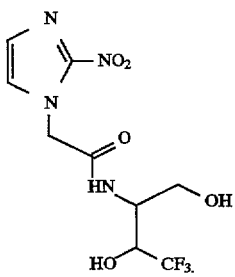

28. A compound having the structural formula (VI)

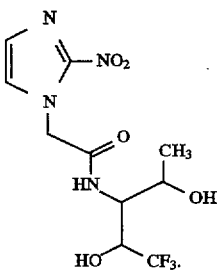

29. A compound having the structural formula (VIII)

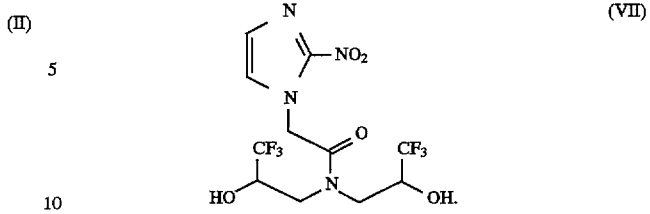

30. A pharmaceutical composition for detecting hypoxic tumor cells, comprising, in combination with a pharmaceutically acceptable carrier, an effective tumor-detecting amount of the compound of claim 1.

31. A pharmaceutical composition for detecting hypoxic tumor cells, comprising, in combination with a pharmaceutically acceptable carrier, an effective tumor-detecting amount of the compound of claim 24.

32. A pharmaceutical composition for detecting hypoxic tumor cells, comprising, in combination with a pharmaceutically acceptable carrier, an effective tumor-detecting amount of the compound of claim 26.

33. A pharmaceutical composition for detecting hypoxic tumor cells, comprising, in combination with a pharmaceutically acceptable carrier, an effective tumor-detecting amount of the compound of claim 5.

34. A pharmaceutical composition for detecting hypoxic tumor cells, comprising, in combination with a pharmaceutically acceptable carrier, an effective tumor-detecting amount of the compound of claim 25.

35. A pharmaceutical composition for detecting hypoxic tumor cells, comprising, in combination with a pharmaceutically acceptable carrier, an effective tumor-detecting amount of the compound of claim 27.

36. A pharmaceutical composition for detecting hypoxic tumor cells, comprising, in combination with a pharmaceutically acceptable carrier, an effective tumor-detecting amount of the compound of claim 28.

37. A pharmaceutical composition for detecting hypoxic tumor cells, comprising, in combination with a pharmaceutically acceptable carrier, an effective tumor-detecting amount of the compound of claim 29.

38. A method for detecting hypoxic tumor cells in a mammalian individual, comprising administering to the individual an effective tumor-detecting amount of the compound of claim 1; and detecting any of said compound associated with and retained by tumor cells present in the mammalian individual.

39. A method for detecting hypoxic tumor cells in a mammalian individual, comprising administering to the individual an effective tumor-detecting amount of the compound of claim 24; and detecting any of said compound associated with and retained by tumor cells present in the mammalian individual.

40. A method for detecting hypoxic tumor cells in a mammalian individual, comprising administering to the individual an effective tumor-detecting amount of the compound of claim 26; and detecting any of said compound associated with and retained by tumor cells present in the mammalian individual.

41. The method of claim 38, wherein the detecting is carried out by magnetic resonance imaging.

42. The method of claim 38, wherein the detecting is carried out using magnetic resonance spectroscopy.

43. A method for detecting hypoxic tumor cells in a mammalian individual, comprising administering to the individual an effective tumor-detecting amount of the compound of claim 5; and detecting any of said compound associated with and retained by tumor cells present in the mammalian individual.

44. A method for detecting hypoxic tumor cells in a mammalian individual, comprising administering to the individual an effective tumor-detecting amount of the compound of claim 25; and detecting any of said compound associated with and retained by tumor cells present in the mammalian individual.

45. A method for detecting hypoxic tumor cells in a mammalian individual, comprising administering to the individual an effective tumor-detecting amount of the compound of claim 27; and detecting any of said compound associated with and retained by tumor cells present in the mammalian individual.

46. A method for detecting hypoxic tumor cells in a mammalian individual, comprising administering to the individual an effective tumor-detecting amount of the compound of claim 28; and detecting any of said compound associated with and retained by tumor cells present in the mammalian individual.

47. A method for detecting hypoxic tumor cells in a mammalian individual, comprising administering to the individual an effective tumor-detecting amount of the compound of claim 29; and detecting any of said compound associated with and retained by tumor cells present in the mammalian individual.

* * * * *